(12) United States Patent
Bozung

(10) Patent No.: US 10,568,640 B2
(45) Date of Patent: Feb. 25, 2020

(54) SURGICAL INSTRUMENT WITH TELESCOPING NOSE MECHANISM

(71) Applicant: STRYKER CORPORATION, Kalamazoo, MI (US)

(72) Inventor: Timothy J. Bozung, Scotts, MI (US)

(73) Assignee: Stryker Corporation, Kalamazoo, MI (US)

( * ) Notice: Subject to any disclaimer, the term of this patent is extended or adjusted under 35 U.S.C. 154(b) by 415 days.

(21) Appl. No.: 15/365,022

(22) Filed: Nov. 30, 2016

(65) Prior Publication Data

US 2017/0150975 A1    Jun. 1, 2017

Related U.S. Application Data

(60) Provisional application No. 62/260,851, filed on Nov. 30, 2015.

(51) Int. Cl.
*A61B 17/16* (2006.01)
*A61B 17/32* (2006.01)
(Continued)

(52) U.S. Cl.
CPC ........ *A61B 17/1617* (2013.01); *A61B 17/162* (2013.01); *A61B 17/1613* (2013.01); *A61B 17/1622* (2013.01); *A61B 17/1624* (2013.01); *A61B 17/1626* (2013.01); *A61B 17/1628* (2013.01); *A61B 17/32002* (2013.01); *A61B 34/20* (2016.02); *A61B 34/25* (2016.02);
(Continued)

(58) Field of Classification Search
CPC ............ A61B 17/1613; A61B 17/1617; A61B 17/162; A61B 17/1622; A61B 17/1624; A61B 17/1626; A61B 17/1628; A61B 17/23002; A61B 2017/00398; A61B 2017/00991; A61B 34/20; A61B 34/25; A61B 2034/2055; A61B 2034/2057; A61B 2034/2059; F16H 25/2056; F16H 2025/2053; F15H 25/20
USPC ........................................................ 74/89.27
See application file for complete search history.

(56) References Cited

U.S. PATENT DOCUMENTS 3,847,154 A * 11/1974 Nordin ............... A61B 17/1622
606/180
5,888,200 A * 3/1999 Walen ................ A61B 17/1622
606/167

(Continued)

OTHER PUBLICATIONS

International Search Report for application No. PCT/US2016/064128, dated May 30, 2017; 12 pages.

*Primary Examiner* — Victor L MacArthur
*Assistant Examiner* — Joseph Brown
(74) *Attorney, Agent, or Firm* — Howard & Howard Attorneys PLLC

(57) ABSTRACT

A surgical instrument comprises a hand-held portion configured to be manipulated by a user and a pivoting portion operatively coupled to the hand-held portion. The pivoting portion is configured to pivot with respect to the hand-held portion according to first and second degrees of freedom. The pivoting portion includes a telescoping nose mechanism including a nose tube, an intermediate unit having a carriage extending from the nose tube to enable linear translation of the nose tube, and a drive motor cooperating with the carriage to linearly translate the nose tube relative to the hand-held portion with respect to a third degree of freedom.

21 Claims, 30 Drawing Sheets

(51) Int. Cl.
  *A61B 34/00* (2016.01)
  *A61B 34/20* (2016.01)
  *F16H 25/20* (2006.01)
  *A61B 17/00* (2006.01)
(52) U.S. Cl.
  CPC ............ *A61B 2017/00398* (2013.01); *A61B 2017/00991* (2013.01); *A61B 2034/2055* (2016.02); *A61B 2034/2057* (2016.02); *A61B 2034/2059* (2016.02); *F16H 2025/2053* (2013.01)

(56) References Cited

U.S. PATENT DOCUMENTS

| | | | | |
|---|---|---|---|---|
| 6,017,354 | A * | 1/2000 | Culp | A61B 17/1626 604/22 |
| 7,422,582 | B2 | 9/2008 | Malackowski et al. | |
| 7,725,162 | B2 | 5/2010 | Malackowski et al. | |
| 9,342,632 | B2 | 5/2016 | Zoran et al. | |
| 9,566,121 | B2 * | 2/2017 | Staunton | F16J 15/3256 |
| 10,005,312 | B2 | 6/2018 | Zoran et al. | |
| 2002/0058958 | A1 * | 5/2002 | Walen | A61B 17/1615 606/170 |
| 2003/0023256 | A1 * | 1/2003 | Estes | A61B 17/162 606/167 |
| 2007/0021752 | A1 * | 1/2007 | Rogers | A61B 17/162 606/80 |
| 2007/0250111 | A1 * | 10/2007 | Lu | A61B 17/221 606/205 |
| 2008/0015084 | A1 * | 1/2008 | Mayumi | F16H 25/20 476/67 |
| 2008/0134812 | A1 * | 6/2008 | Murata | F16H 25/20 74/25 |
| 2009/0326537 | A1 * | 12/2009 | Anderson | A61B 17/1624 606/80 |
| 2010/0063524 | A1 * | 3/2010 | McCombs | A61B 17/162 606/167 |
| 2012/0071752 | A1 | 3/2012 | Sewell et al. | |
| 2013/0060278 | A1 * | 3/2013 | Bozung | A61B 17/32002 606/205 |
| 2013/0096574 | A1 * | 4/2013 | Kang | A61B 17/1622 606/130 |
| 2013/0123783 | A1 * | 5/2013 | Marczyk | A61B 17/29 606/45 |
| 2014/0276943 | A1 | 9/2014 | Bozung et al. | |
| 2015/0119889 | A1 * | 4/2015 | Prescott | A61B 17/1679 606/80 |
| 2015/0182285 | A1 * | 7/2015 | Yen | G05B 15/02 606/80 |

\* cited by examiner

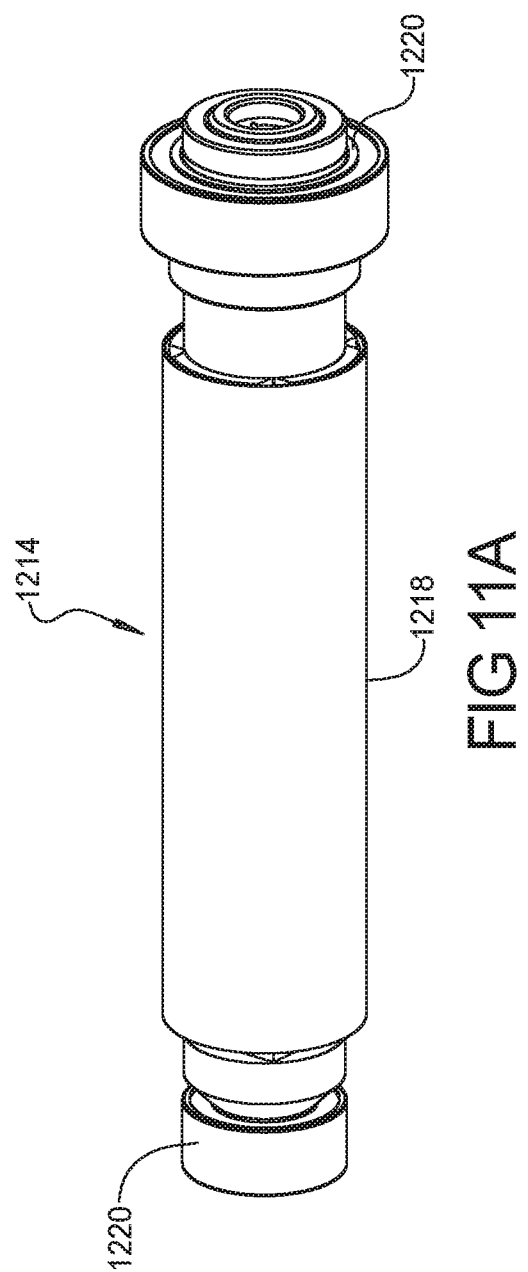

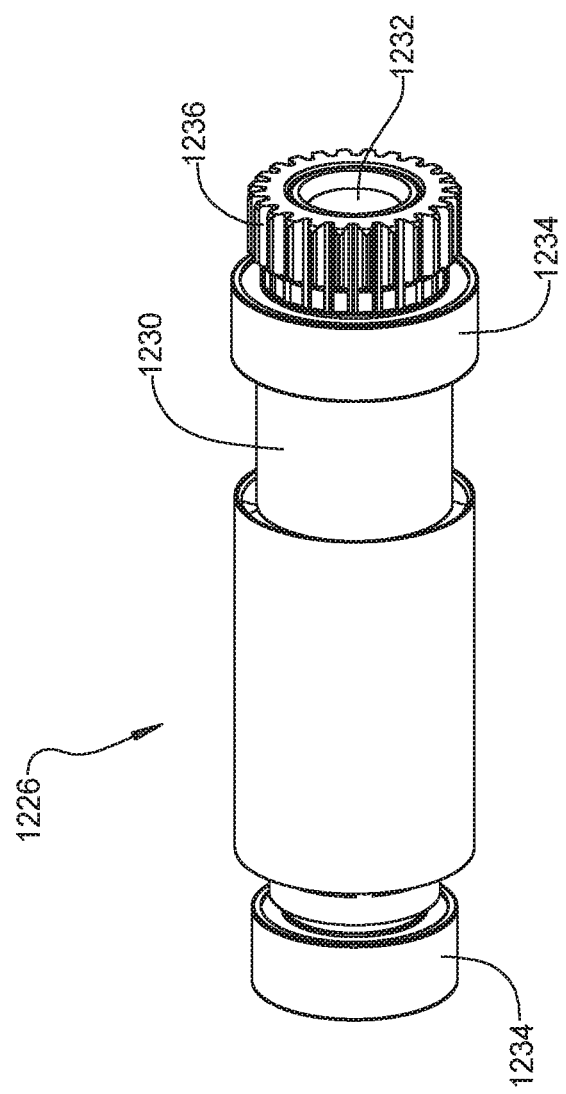

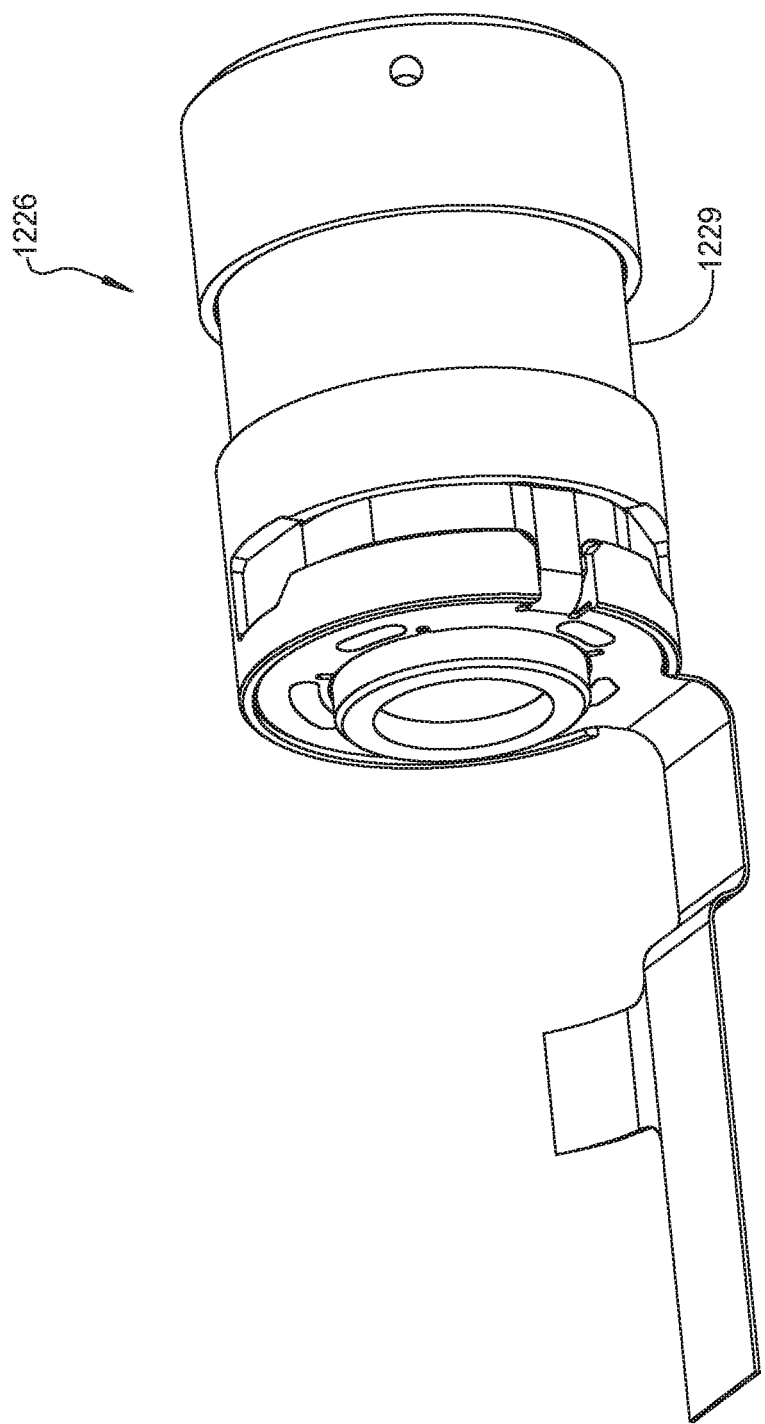

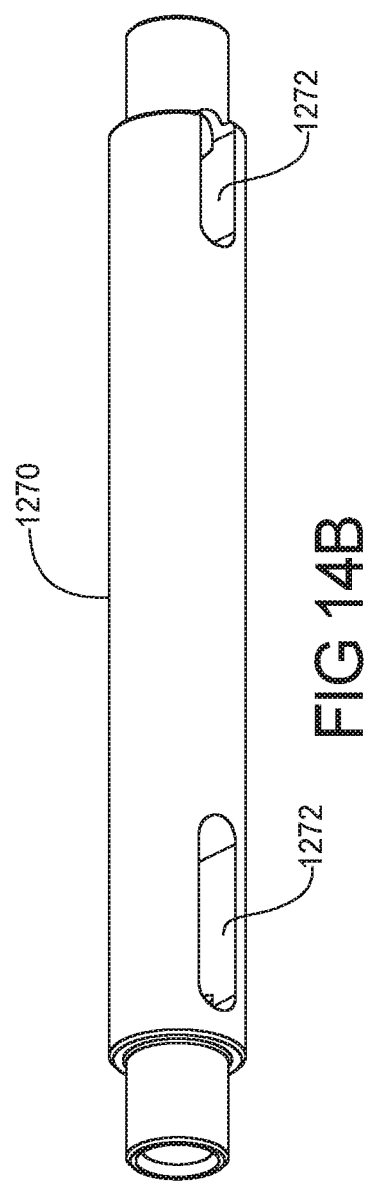
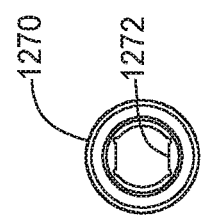

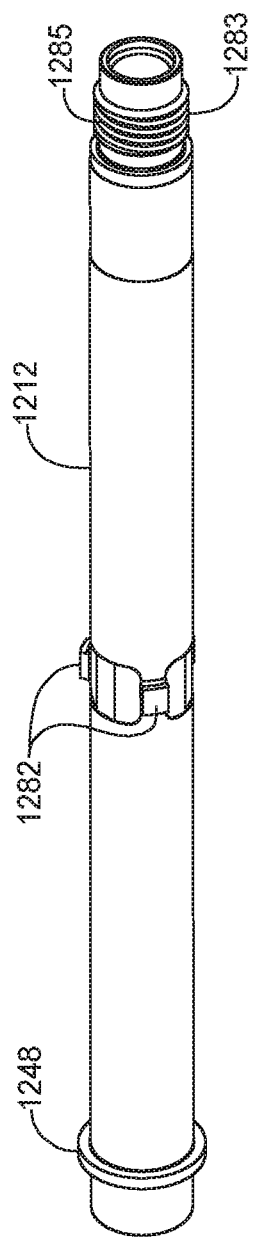

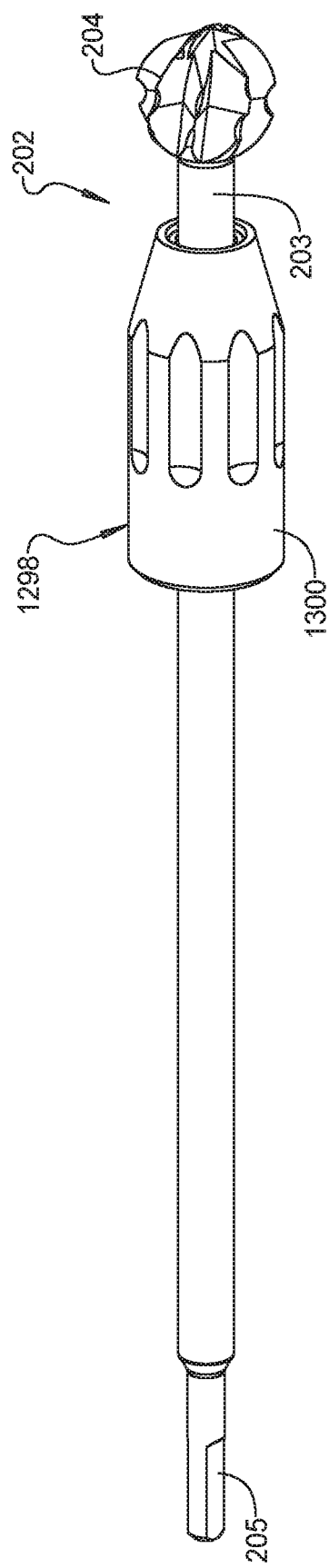

SURGICAL INSTRUMENT WITH TELESCOPING NOSE MECHANISM

CROSS-REFERENCE TO RELATED APPLICATION

The subject application claims the benefit of U.S. provisional patent application No. 62/260,851, filed Nov. 30, 2015, the disclosure of which is hereby incorporated by reference in its entirety.

TECHNICAL FIELD

The present disclosure relates generally to surgical instruments and, more particularly, to a surgical instrument with a telescoping nose mechanism for use in a system for tracking and controlling the surgical instrument.

BACKGROUND

Tracking systems (also known as navigation systems) assist surgeons during surgeries that require the precise locating of instruments such as surgical instruments. Such surgeries include neurosurgery, spine, and orthopedic surgery. In one implementation, the tracking system tracks a position and orientation of the surgical instrument during the surgical procedure and often displays the position and/or orientation of the instrument on a monitor in conjunction with a preoperative image or an intraoperative image of the patient (preoperative images are typically prepared by MRI or CT scans, while intraoperative images may be prepared using a fluoroscope, low level x-ray or any similar device).

It has also been proposed that the surgical instrument be used free hand without the aid of a cutting jig, guide arm or other constraining mechanism to establish the location to which the cutting implement at the end of the instrument is applied. See, for example, U.S. Pat. No. 6,757,582 to Brisson et al. In one implementation, the tracking system typically employs a camera that detects a tracking device located on the surgical instrument. The tracking device has a plurality of optical markers such as light emitting diodes (LEDs) to determine the position and orientation of the surgical instrument. The position of the surgical instrument usually correlates to the coordinates of a working end of the instrument in three-dimensional space, the x, y, z or Cartesian coordinates, relative to the camera. The orientation of the surgical instrument means the pitch, roll, and yaw of the instrument. When both the position and the orientation of the surgical instrument are defined, the relative position of that instrument is known to the tracking system.

One type of surgical instrument is known as a "pencil-style" hand-held surgical instrument. The pencil-style hand-held surgical instrument is held by the hand of the user to perform a medical/surgical task on the tissue of the patient such as shape or remove tissue such as bone from a femur. The pencil-style handheld surgical instrument makes use of a telescoping nose for a depth degree of freedom. The pencil-style hand-held surgical instrument also makes use of two additional degrees of freedom which are provided via a pivoting gimbal mechanism. In one implementation, the instrument includes a portion having a threaded nose tube that translates linearly. A motor telescopes the nose tube using an elongated rotor with a long internal thread directly engaging the nose tube. The nose tube has an external thread on a proximal end, which directly interfaces with the rotor of the motor. As the rotor spins in one direction, the nose tube pulls in (due to the nose tube being keyed) and spinning in the opposite direction results in the nose tube pushing out. An example of such a pencil-style hand-held surgical instrument is disclosed in pending patent application U.S. Patent Application Publication No. 2013/0060278, filed Aug. 31, 2012, the entire disclosure of which is hereby expressly incorporated by reference.

Although the above has worked well, it is desirable to improve hand-held surgical instruments.

SUMMARY

One embodiment of a surgical instrument is provided. The surgical instrument comprises a hand-held portion configured to be manipulated by a user and a pivoting portion operatively coupled to the hand-held portion. The pivoting portion is configured to pivot with respect to the hand-held portion according to first and second degrees of freedom. The pivoting portion includes a telescoping nose mechanism including a nose tube, an intermediate unit having a carriage extending from the nose tube to enable linear translation of the nose tube, and a drive motor cooperating with the carriage to linearly translate the nose tube relative to the hand-held portion with respect to a third degree of freedom.

Another embodiment of a surgical instrument is provided. The surgical instrument comprises a nose tube, a drive motor including a drive gear, and an intermediate unit coupled between the nose tube and the drive motor. The intermediate unit includes a plurality of leadscrews each being threaded and having a driven gear at one end. The intermediate unit includes a carriage being threaded for interfacing with the leadscrews. The drive gear is configured to interface with each of the driven gears to enable rotation of each of the leadscrews such that the carriage linearly translates along the leadscrews to enable telescoping of the nose tube.

Yet another embodiment of a surgical instrument is provided. The surgical instrument comprises a pivoting portion and a shaft disposed in the pivoting portion. A first drive motor is disposed in the pivoting portion and is configured to rotate the shaft. A second drive motor is disposed in the pivoting portion and is configured to linearly translate the shaft. The second drive motor includes a rotor and a drive gear each defining an aperture extending therethrough to receive the shaft and to enable the shaft to freely rotate and linearly translate therethrough.

BRIEF DESCRIPTION OF THE DRAWINGS

Other advantages of the present disclosure will be readily appreciated as the same becomes better understood by reference to the following detailed description when considered in connection with the accompanying drawings wherein:

FIG. 11A is a perspective view of a bur drive rotor of the drill portion of FIG. 3;

FIG. 12 is a perspective view of a rotor of a linear drive motor of the drill portion of FIG. 4 and FIG. 9;

FIG. 13 is a perspective view of a coil of the linear drive motor of FIG. 4;

FIG. 14A is an end view of a bur shaft of the drill portion of FIG. 6;

FIG. 14B is a perspective view of the bur shaft of FIG. 6;

FIG. 16B is another perspective view of the nose tube of FIG. 16A incorporating a threaded insert;

FIG. 18A is a perspective view of an accessory of the of the drill portion of FIG. 2;

DETAILED DESCRIPTION

Figure 1A:
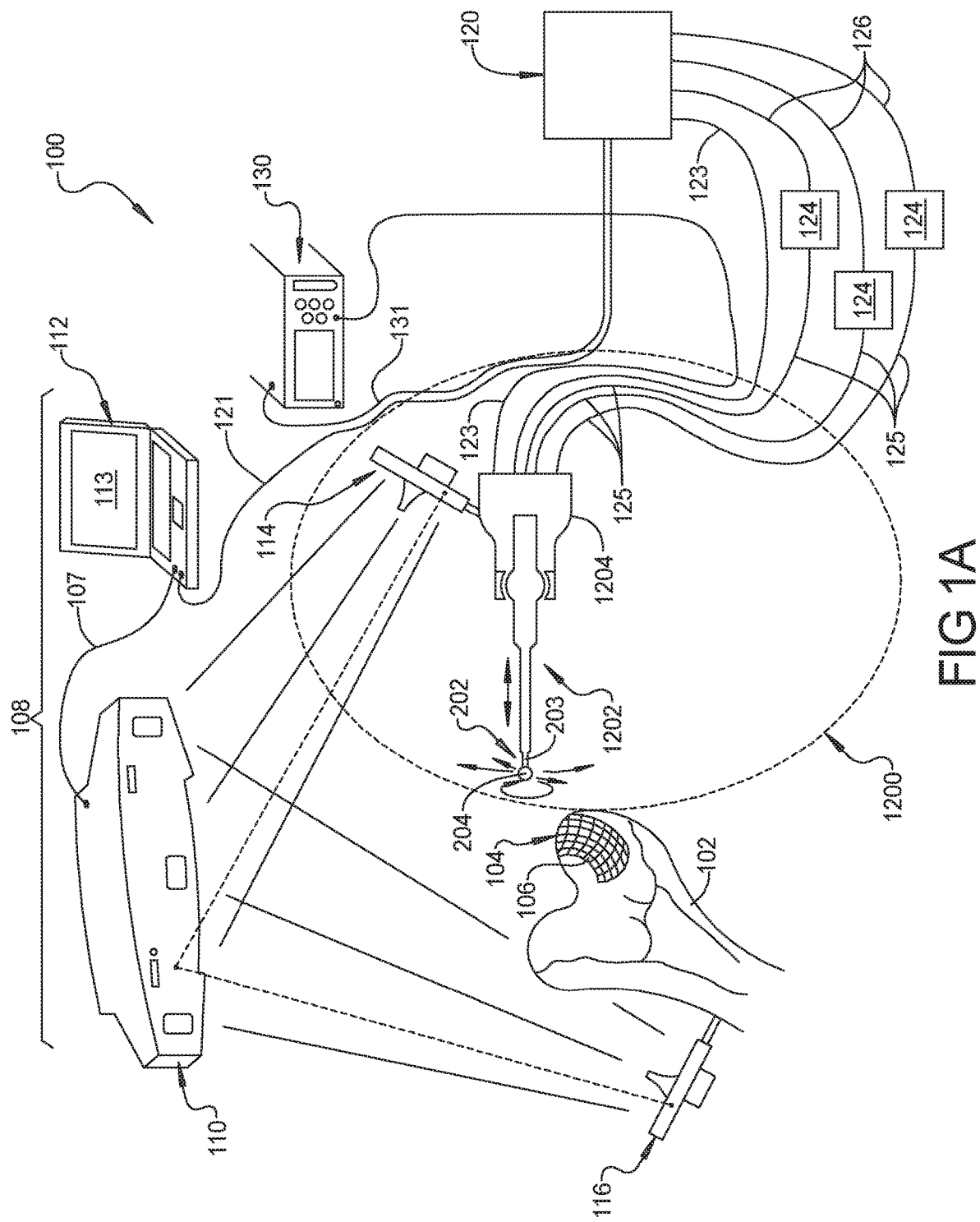
FIG. 1A is a schematic view of one embodiment of a tracking and control system for a surgical instrument.
Figure 1B:
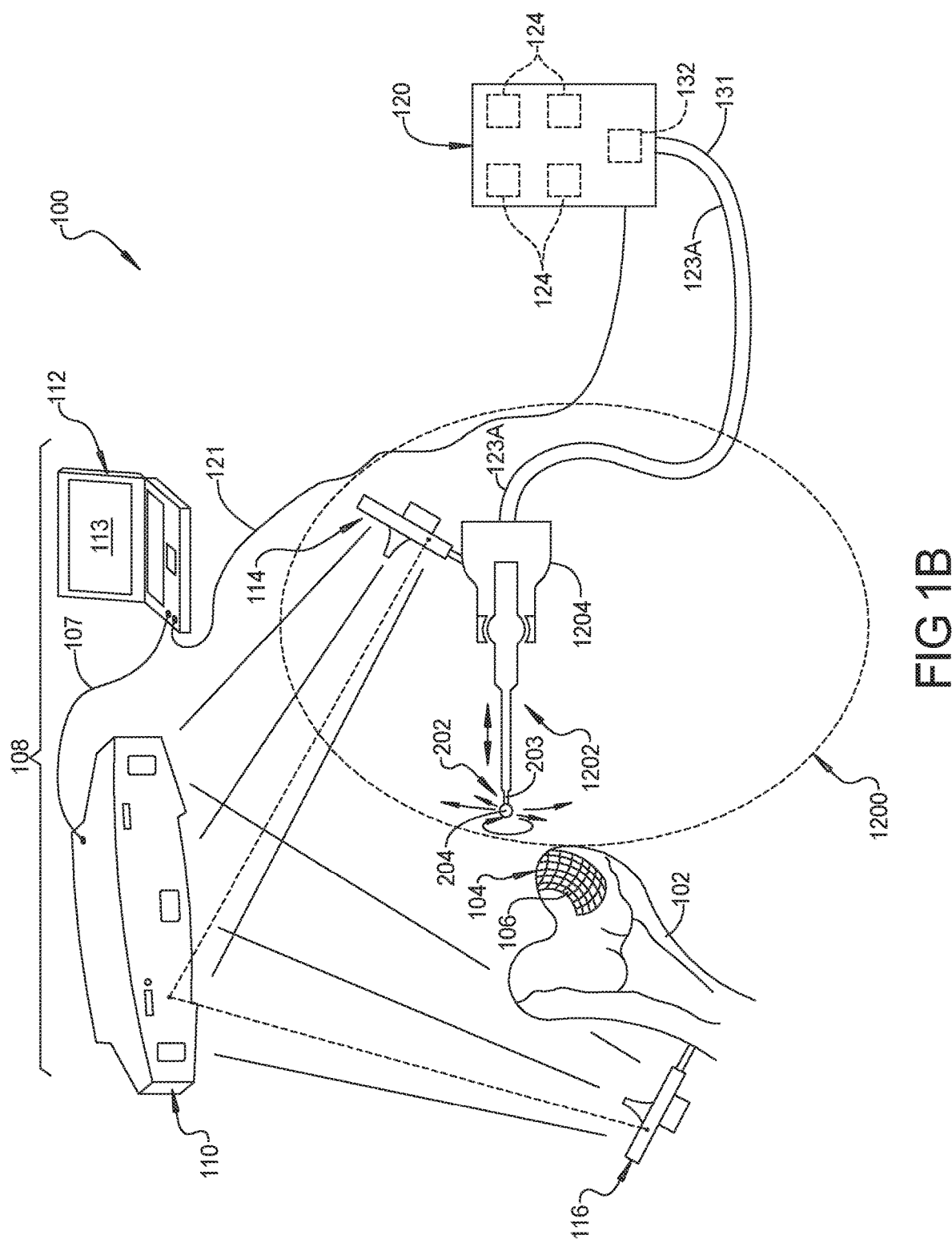
FIG. 1B is a schematic view of another embodiment of a tracking and control system for a surgical instrument.
Figure 18B:
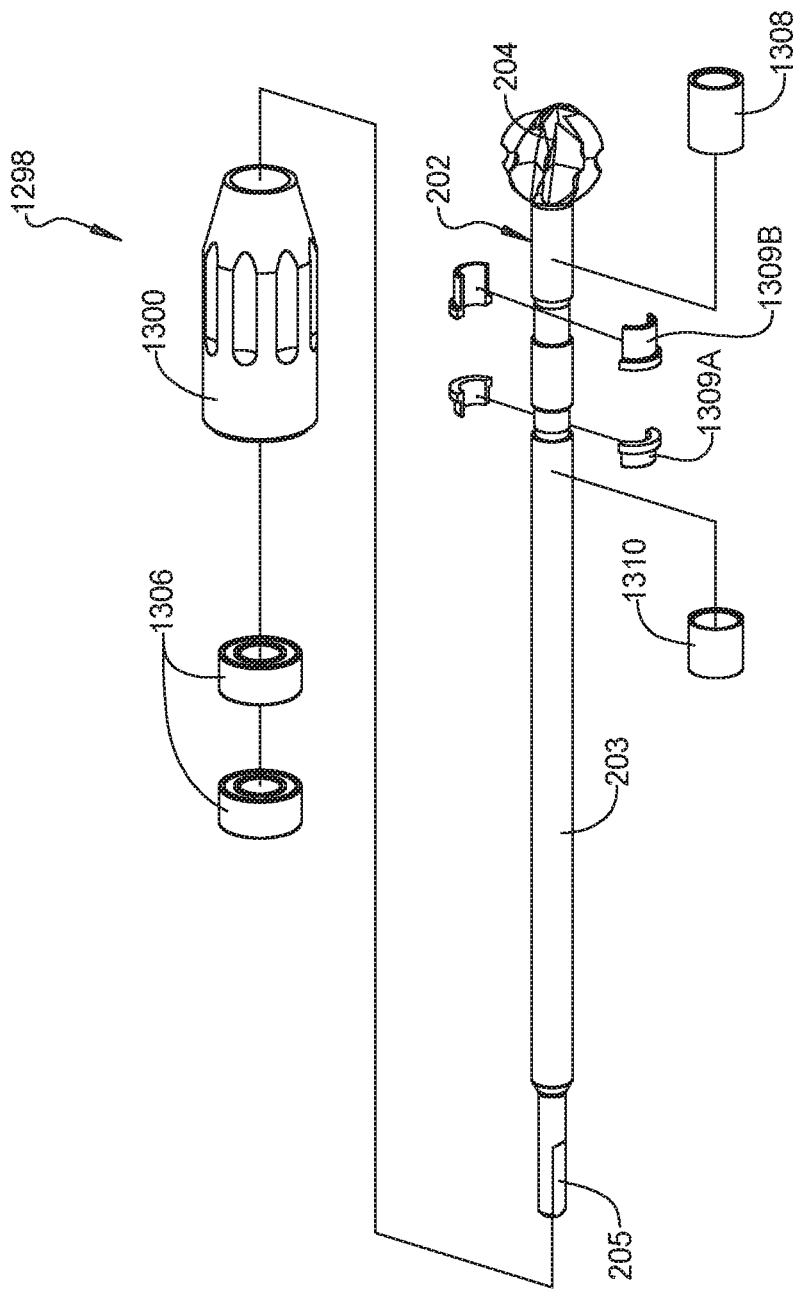
FIG. 18B is an exploded view of the accessory of FIG. 18A.

Referring to FIGS. 1A and 1B, a tracking and control system 100 used in conjunction with a surgical instrument 1200, according to one embodiment, is shown. The surgical instrument 1200 is used with an accessory 202. In one embodiment, the accessory 202 has a rotatable shaft 203 and a distal end tip 204 at one end of the shaft 203. The accessory 202 is the component that performs a medical/surgical task or procedure on tissue of a patient. The types of accessories 202 that can be driven by the surgical instrument 1200 include shavers, drill bits, burs, ultrasonic tools, material delivery accessories, measurement devices, imaging accessories, or the like. In FIGS. 1A and 1B, the depicted accessory 202 is a bur (cutting accessory) that has at its distal end 204 a spherical bur head for removing bone and a proximal end 205 having a keyed double-D shape as illustrated in FIGS. 18A and 18B.

The surgical instrument 1200 rotates the shaft 203 and distal end tip 204 of the accessory 202 and the tracking and control system 100 tracks the surgical instrument 1200 to keep the distal end tip 204 of the accessory 202 that is attached to the instrument 1200 in a desired relationship to a predefined boundary. (Here "distal" means away from the user holding the surgical instrument 1200 and towards the tissue to which the instrument is applied. "Proximal" means towards the user holding the surgical instrument 1200 and away from the tissue to which the instrument is applied.) The tracking and control system 100 controls the position of the distal end tip 204 of the accessory 202 relative to a home position on the surgical instrument 1200. It should be appreciated that this control prevents the distal end tip 204 of the accessory 202 from colliding with or breaching a boundary at the surgical site to which the accessory 202 is applied.

Figure 2:
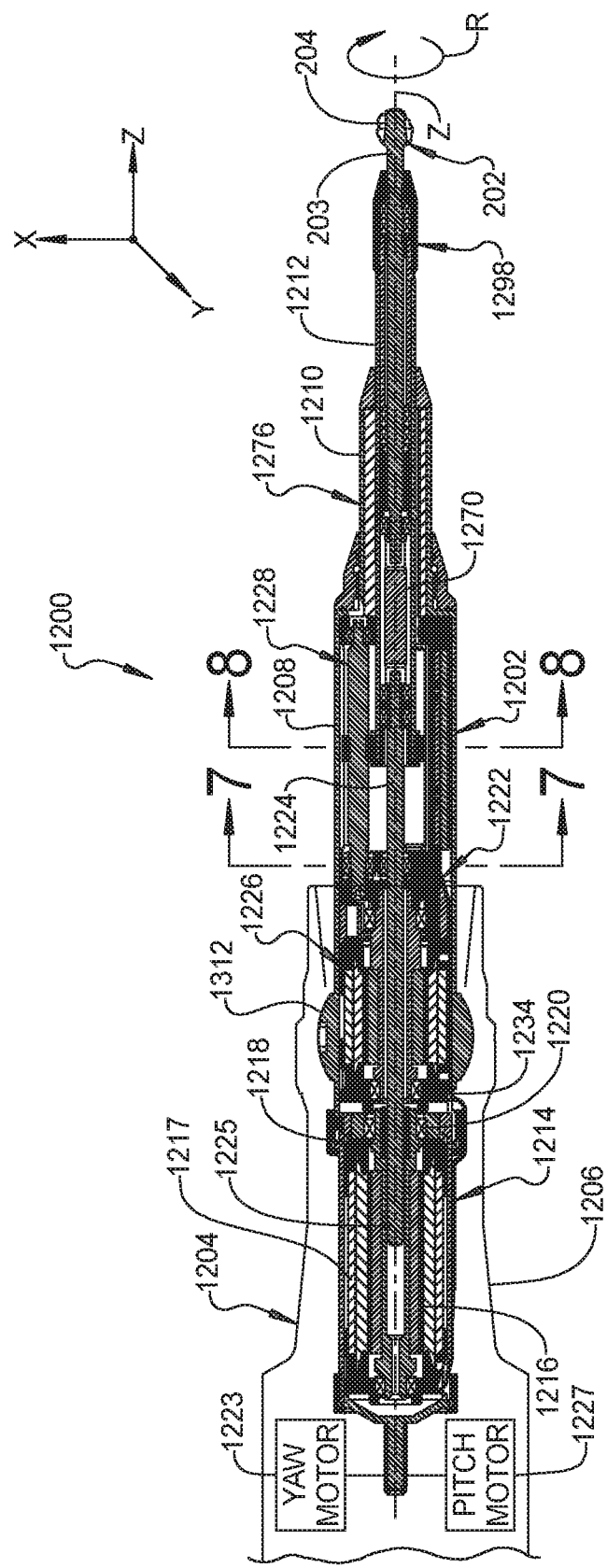
FIG. 2 is a cross-sectional view of a drill portion of the surgical instrument used in the tracking and control system of FIGS. 1A and 1B.
Figure 3:
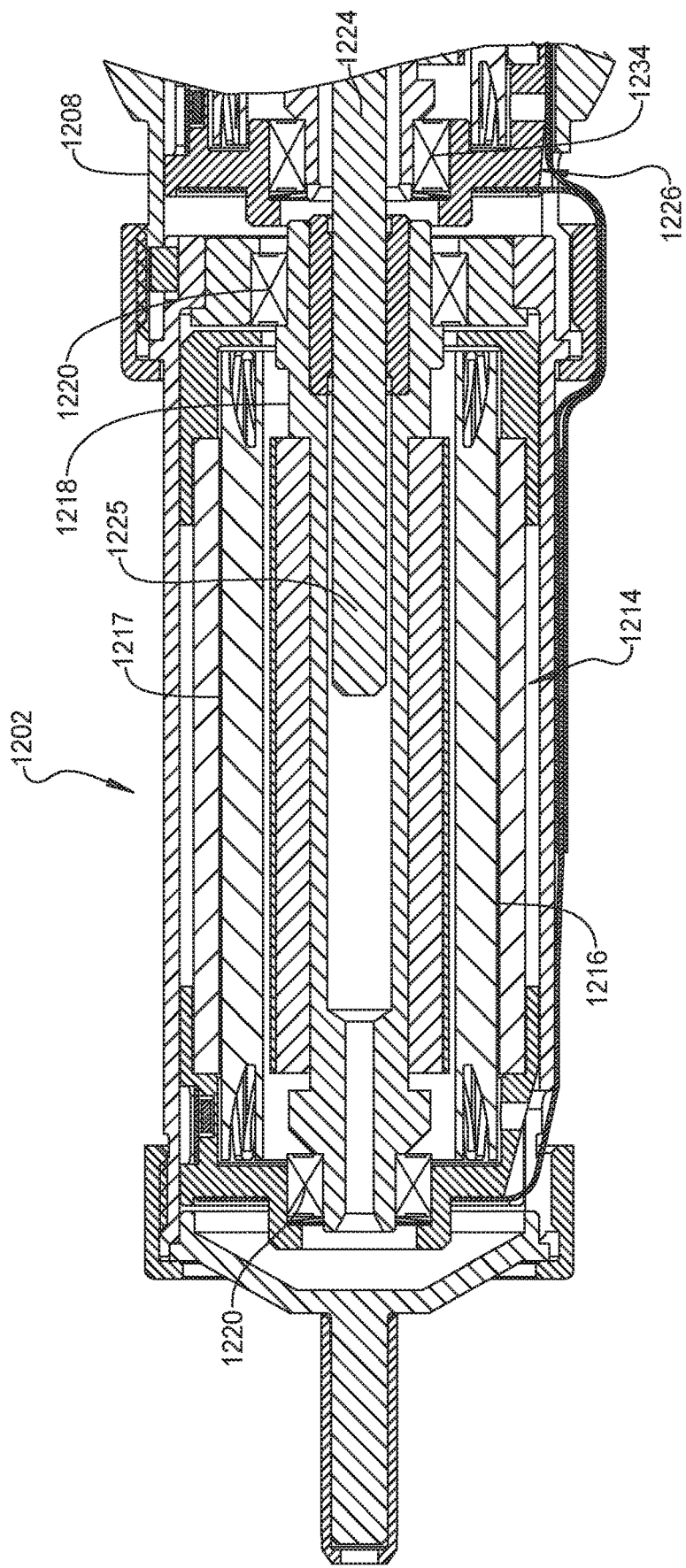
FIG. 3 is an enlarged cross-sectional view of a portion of the surgical instrument of FIG. 2.
Figure 4:
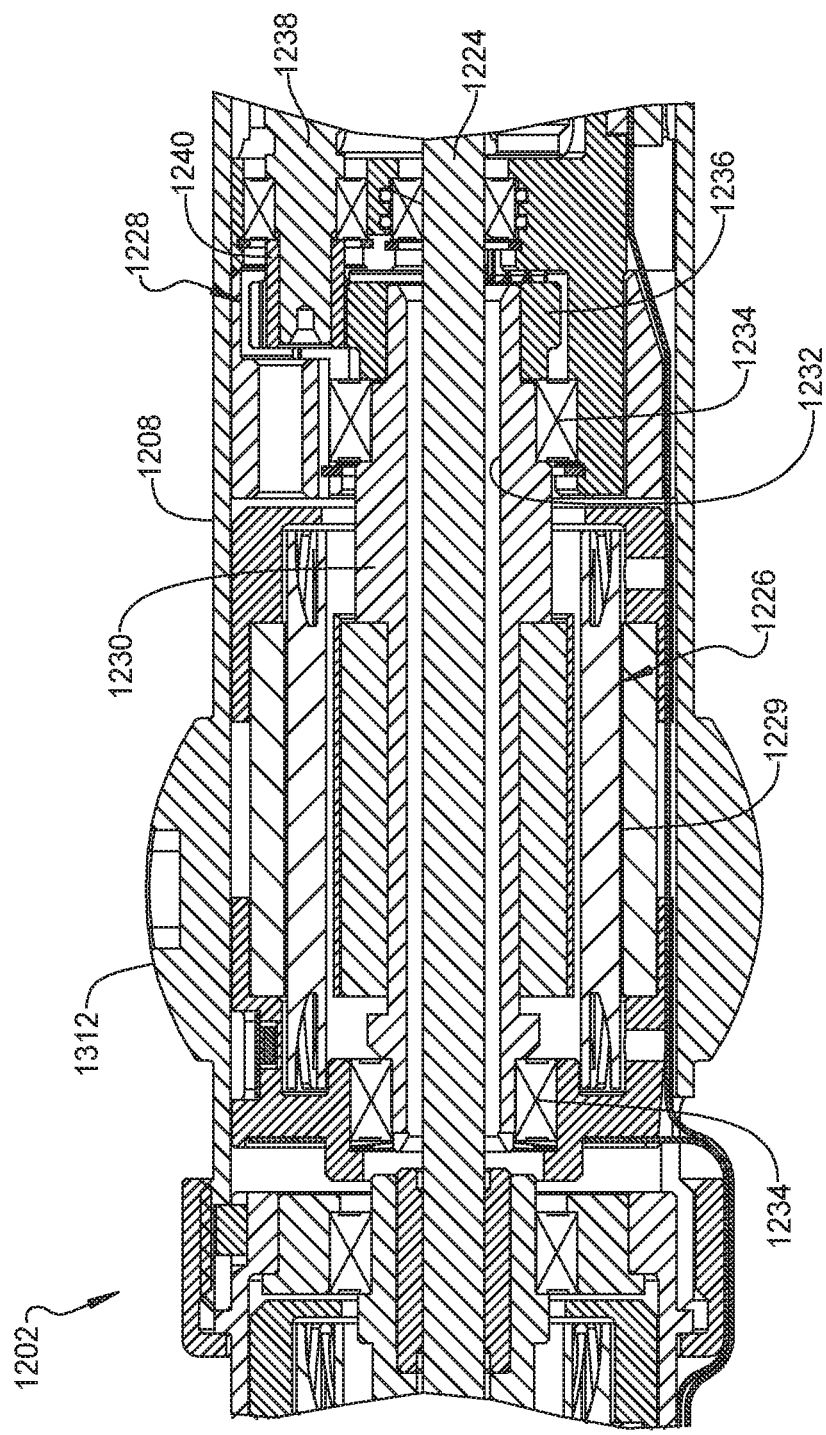
FIG. 4 is an enlarged cross-sectional view of another portion of the surgical instrument of FIG. 2.

In one embodiment, the surgical instrument 1200 has a hand-held configuration. The hand-held configuration shown is a pencil-grip configuration. However, other types of hand-held configurations may also employ the concepts described herein. The surgical instrument 1200 includes a drill portion (also referred to as a pivoting portion), generally indicated at 1202, for example, referenced in FIGS. 2-6, coupled to the accessory 202, and a hand-held portion 1204 held by the hand of the user, which provides two pivoting degrees of freedom of the drill portion 1202. In some embodiments where the accessory 202 rotates, e.g., a bur, a drill bit, etc., the drill portion 1202 rotates the accessory 202 about a rotational axis R (FIG. 2).

As set forth further below, with respect to the surgical instrument 1200, the rotational axis R moves relative to the hand-held portion 1204 in pitch and yaw. The drill portion 1202 telescopes the accessory 202 along a linear or depth axis Z relative to the home position. With respect to the drill portion 1202, it should be appreciated that, in the embodiment illustrated, the depth axis "Z" and the rotational axis "R" are the same axis.

As illustrated in FIGS. 1A and 1B, the surgical instrument 1200 and accessory 202 are shown being used to shape a portion of a femur 102. It should be appreciated that the surgical instrument 1200 can be used to remove or otherwise treat other types of tissue, including soft tissue as well as other bones of the human body.

With continued reference to FIGS. 1A and 1B, in the embodiment shown, the femur 102 has a target volume 104 of material that is to be removed by the distal end tip 204. The target volume 104 is defined by a boundary called the work boundary 106. This work boundary 106 defines the surface of the bone that should remain after the procedure. The tracking and control system 100 tracks and controls the surgical instrument 1200 to ensure that the distal end tip 204 only removes the target volume 104 of material and does not extend beyond the work boundary 106. It should be appreciated that the work boundary 106 in other embodiments may be defined by any shape or size and may include 2-D or 3-D shapes, lines, trajectories, surfaces, linear paths, non-linear paths, volumes, planes, bore holes, contours, and the like. In some embodiments, the work boundary 106 can define a 2-D or 3-D boundary across which the surgical instrument 1200 should not cross. In other embodiments, the work boundary 106 may define a line, path, trajectory or course along which the accessory 202 of the surgical instrument 1200 should travel. It should be appreciated that, in these cases, the work boundary 106 is also referred to as a work path, work trajectory or work course.

Referring to FIGS. 1A and 1B, the tracking and control system 100 includes a navigation unit 108. The navigation unit 108 tracks the positions and orientations of the femur 102 and surgical instrument 1200. The navigation unit 108 includes a camera 110 and a navigation computer 112 that receives and processes signals from the camera 110. The camera 110 is connected to the navigation computer 112 by a data connection 107. In one implementation, the data connection 107 may be an IEEE 1394 interface, which is a serial bus interface standard for high-speed communications and isochronous real-time data transfer. It should be appreciated that the data connection 107 could also use a company specific protocol.

One camera 110 that can be incorporated into the tracking and control system 100 is the FlashPoint® 6000 Camera sold by Stryker Corporation of Kalamazoo, Mich. The camera 110 includes three separate high resolution CCD cameras (not shown). The CCD cameras detect infrared (IR) signals. The camera 110 is mounted to a stand (not shown) to position the camera 110 above the zone in which the procedure is to take place to provide the camera 110 with a field of view of trackers 114 and 116 attached to the hand-held portion 1204 and femur 102, respectively, that, ideally, is free from obstructions. Each tracker 114 and 116 has a plurality of optical markers in the form of light emitting diodes, such as three LEDs (not shown), that transmit infrared light to the camera 110. In some cases, the optical markers are three or more light reflectors (not shown) for use with a camera unit (not shown) that transmits light that reflects off the light reflectors. It should be appreciated that, in other procedures, additional trackers may be affixed to other bones, tissue, or other parts of the body, tools, or equipment. It should be appreciated that the trackers 114 and 116 may also be referred to as tracking devices 114 and 116, respectively.

The navigation computer 112 can be a personal computer such as a laptop computer. The navigation computer 112 has a display 113, central processing unit (not shown), memory (not shown), and storage (not shown). The navigation computer 112 is loaded with software. The software converts the signals received from the camera 110 into data representative of the position and orientation of the objects to which trackers 114 and 116 are attached. Also associated with the navigation computer 112 is an input device, such as a mouse or other suitable pointer-input device and keyboard.

Based on the light captured signals forwarded from the camera 110, the navigation computer 112 determines the position of each optical marker and thus the position and orientation of the objects to which they are attached relative to the camera 110. An example of the camera 110, navigation computer 112, and trackers 114, 116 are shown in U.S. Pat. No. 7,725,162 to Malackowski et al., the disclosure of which is hereby incorporated by reference, including the camera, navigation computer and trackers and associated methods of operation and use disclosed therein.

The tracking and control system 100 includes an instrument controller 120 in communication with the navigation computer 112 via a data connection 121. In FIGS. 1A and 1B, the instrument controller 120 may be or may include a computer. The data connection 121 may be an IEEE 1394 interface, which is a serial bus interface standard for high-speed communications and isochronous real-time data transfer. In another implementation, the data connection 121 could use a company specific protocol. The instrument controller 120 communicates with the surgical instrument 1200 by a data connection 123. It should be appreciated that, in some implementations, the navigation computer 112 and instrument controller 120 may be a single unit.

In FIG. 1A, the tracking and control system 100 includes a plurality of motor controllers 124 in communication with each of a plurality of motors of the surgical instrument 1200 via motor power connections 125. In addition, the instrument controller 120 is in communication with the motor controllers 124 via data connections 126. The data connection 126 may be a high-speed data communication protocol such as EtherCat. In another implementation, the data connection 126 could use a company specific protocol. The motor controllers 124 power and position actuators of the surgical instrument 1200 via the motor power connections 125. It should be appreciated that, in some implementations, the motor controllers 124 may be a single unit.

In the embodiment illustrated in FIG. 1A, the tracking and control system 100 may further include an instrument driver 130. The instrument driver 130 provides power to an accessory drive motor to be described of the drill portion 1202 to control the power and/or speed of the accessory 202. The power supply and control components internal to instrument driver 130 may be similar those in the surgical instrument control console described in U.S. Pat. No. 7,422,582, entitled CONTROL CONSOLE TO WHICH POWERED SURGICAL HANDPIECES ARE CONNECTED, THE CONSOLE CONFIGURED TO SIMULTANEOUSLY ENERGIZE MORE THAN ONE AND LESS THAT ALL OF THE HANDPIECES, the disclosure of which is hereby incorporated by reference, including the power supply and control components of the control console and associated methods of operation and use disclosed therein. The instrument driver 130 is in communication with the instrument controller 120 via a data connection 131. The data connection 131 may be an IEEE 1394 interface, which is a serial bus interface standard for high-speed communications and isochronous real-time data transfer. The data connection 131 could use a company specific protocol. It should be appreciated that, in other implementations, the instrument driver 130 could be integrated into or part of the instrument controller 120.

In FIG. 1B, the tracking and control system 100 includes the instrument controller 120 in communication with the navigation computer 112 via a data connection 121. In this embodiment, the instrument controller 120 includes or contains the motor controllers 124 and a power supply 132 for each of the motors of the surgical instrument 1200. It should be appreciated that in this embodiment the instrument driver 130 of the previous embodiment has been replaced by an additional motor controller 124. The instrument controller 120 communicates with the surgical instrument 1200 by a data connection 123A. In the embodiment shown in FIG. 1B, the makeup of the connection 123A may differ from that of FIG. 1A and a common power connection 131 is required to power the plurality of motors of the surgical instrument 1200. This type of embodiment may also impact the type and amount of electronics embedded within the surgical instrument 1200. In addition, this embodiment may significantly reduce the size and number of connections between the surgical instrument 1200 and instrument controller 120. It should be appreciated that the instrument controller 120 may include a personal computer, etc.

Figure 1C:
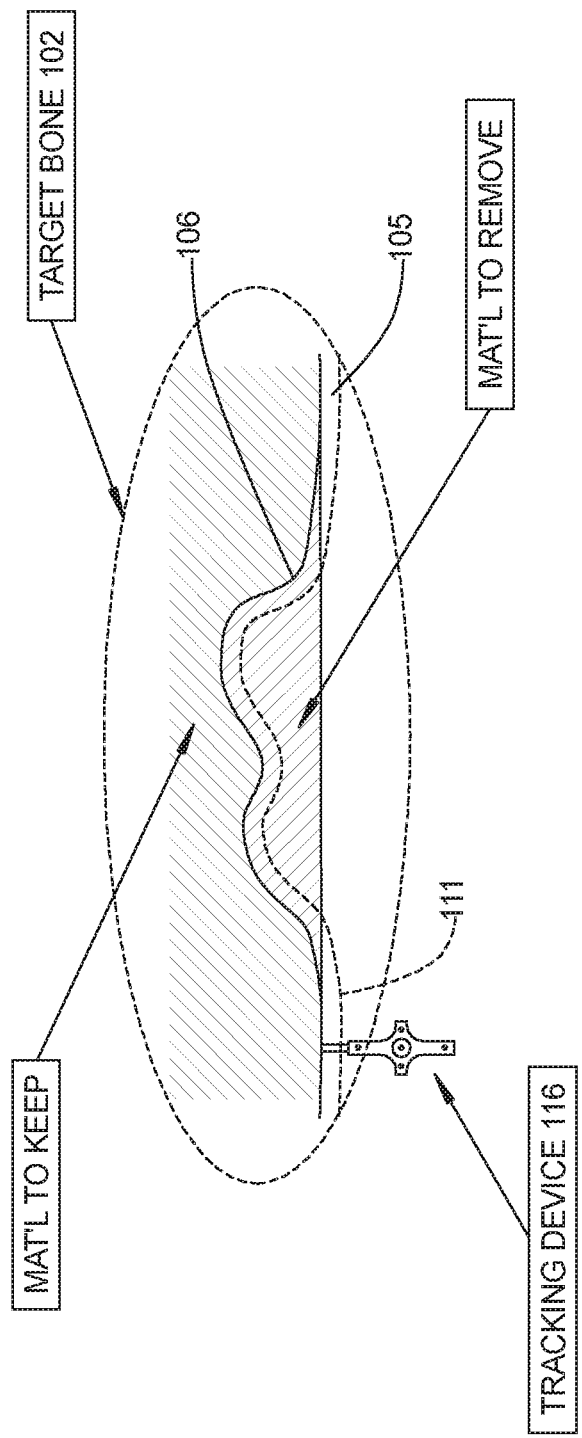
FIG. 1C is an illustration of a work boundary for the surgical instrument of FIGS. 1A and 1B.

Referring to FIG. 1C, the instrument controller 120 defines a constraint boundary 111 that is located a predetermined distance from the work boundary 106 to define a buffer 105. In one implementation of the tracking and control system 100, the instrument controller 120 determines the position of the center of the distal end tip 204, relative to the constraint boundary 111 to control the surgical instrument 1200. The relative distance between the working boundary 106 and the constraint boundary 111 is a function, in part, of the geometry of the accessory 202. For example, if the accessory 202 includes the distal end tip 204 as a spherical bur head, the constraint boundary 111 is one-half the diameter of the bur head. It should be appreciated that, when the centroid of the bur head is on the constraint boundary 111, the bur's outer cutting surface is at the work boundary 106.

Referring to FIGS. 1A and 1B, the surgical instrument 1200 communicates with the instrument controller 120 via the data connection 123. The data connection 123 provides the path for the input and output required to control the surgical instrument 1200 based on the position and orientation data generated by the navigation computer 112 and transmitted to the instrument controller 120. The surgical instrument 1200 can be used in the tracking and control system 100 shown in FIGS. 1A and 1B as described above. As set forth above, the tracking and control system 100 tracks the positions and orientations of the target volume 104 and the surgical instrument 1200 to keep the distal end tip 204 of the accessory 202 at the target volume 104. It should be appreciated that the surgical instrument 1200 typically includes the data connection 123 for connection to the tracking and control system 100, and specifically to the instrument controller 120.

Referring to FIG. 2, the surgical instrument 1200 includes a distal assembly, also referred to as the drill portion 1202, and a proximal assembly, also referred to as the hand-held portion 1204. The hand-held portion 1204 is manipulated by the user, and in some embodiments, manually supported and moved by the user. In some embodiments, the user operates the surgical instrument 1200 by grasping and supporting the hand-held portion 1204 and the surgical instrument 1200 is unsupported by other mechanical arms, frames, etc. In other embodiments, the surgical instrument 1200 may be attached to a robotic arm or manipulator, which in some modes, enables the user to manually interface with the hand-held portion 1204 to control movement of the robotic arm or manipulator. One example of such instrument is described in United States Patent Application Publication No. US2014/0276943, filed Mar. 3, 2014, entitled SYSTEMS AND METHODS FOR ESTABLISHING VIRTUAL CONSTRAINT BOUNDARIES, the entirety of which is incorporated by reference herein. It should be appreciated that the tracking device 114 may be attached to the hand-held portion 1204 for tracking the surgical instrument 1200.

The accessory 202 is movably coupled to the hand-held portion 1204 by the drill portion 1202. The drill portion 1202 releasably holds the accessory 202 and drives the accessory 202 to perform the medical/surgical task on the tissue of the patient, and moves the accessory 202 in the linear or depth axis Z in a depth degree of freedom to prevent the distal end tip 204 of the accessory 202 from colliding with or breaching the work boundary 106 of the target volume 104 to which the accessory 202 is being applied. It should be appreciated that the two pivot degrees-of-freedom, contained within the hand-held portion 1204, work in a coordinated fashion with the above-described linear or depth degree-of-freedom.

The hand-held portion 1204 engages the drill portion 1202 and moves the drill portion 1202 to adjust the pitch and yaw of the accessory 202 to prevent the distal end tip 204 of the accessory 202 from colliding with or breaching the work boundary 106 of the target volume 104. As set forth above, "pitch" is the up-down angular orientation (i.e., the X-axis shown in the Figures) of the drill portion 1202 and accessory 202 relative to a horizontal plane through a center of a gimbal 1312 to be described and "yaw" is the right-left angular orientation (i.e., the Y-axis shown in the Figures) of the drill portion 1202 and accessory 202 relative to a vertical plane through the center of the gimbal 1312. It should be appreciated that the range of motion of the distal end tip 204 of the accessory 202 relative to the drill portion 1202 is defined by the tracking and control system 100.

The hand-held portion 1204 includes an outer casing 1206 and the drill portion 1202 includes an outer casing 1208 that remains rotationally fixed about the Z-axis relative to the outer casing 1206 of the hand-held portion 1204. The drill portion 1202 also includes a bushing casing 1210 fixed to the outer casing 1208 and a movable nose tube 1212 that extends from the bushing casing 1210 and supports the accessory 202. It should be appreciated that the hand-held portion 1204 engages the drill portion 1202 and adjusts the pitch and yaw of the drill portion 1202 relative to the hand-held portion 1204 in the same manner as disclosed in U.S. Patent Application Publication No. 2013/0060278, filed Aug. 31, 2012, entitled "SURGICAL INSTRUMENT INCLUDING HOUSING, A CUTTING ACCESSORY THAT EXTENDS FROM THE HOUSING AND ACTUATORS THAT ESTABLISH THE POSITION OF THE CUTTING ACCESSORY RELATIVE TO THE HOUSING," hereby incorporated by reference herein in its entirety.

Referring to FIGS. 2, 3, 5, 6, 11A, and 11B, the drill portion 1202 includes an accessory drive mechanism, generally indicated at 1214, coupled to the accessory 202 for rotating and providing torque to the accessory 202 about the rotational axis R. The drive mechanism 1214 includes a drive motor 1216, also referred to as an accessory drive motor, disposed in the outer casing 1208 for driving an intermediate shaft 1224, which drives an interconnecting shaft 1270 (also referred to as "bur shaft"), which finally drives the shaft 203 of the accessory 202.

The drill portion 1202 and the accessory 202 move relative to the hand-held portion 1204 in a plurality of degrees of freedom. The surgical instrument 1200 includes a plurality of actuators, e.g., a linear drive motor 1226 to be described, yaw motor 1223, and pitch motor 1227, operatively coupled to the accessory 202 for moving the accessory 202 in a plurality of degrees of freedom relative to the hand-held portion 1204. It should be appreciated that, at least one of the actuators, and more specifically, the yaw motor 1223 and the pitch motor 1227, move the drive mechanism 1214 and the accessory drive motor 1216 in pitch and yaw relative to the hand-held portion 1204. It should also be appreciated that the outer casing 1208 is movable by at least one of the actuators, e.g., the yaw motor 1223 in yaw and the pitch motor 1227 in pitch relative to the hand-held portion 1204. Motors are connected to the motor controllers 124. The linear drive motor 1226 may actuate in a linear or rotational manner. The yaw and pitch motors 1223, 1227 may be like those disclosed in U.S. Patent Application Publication No. 2013/0060278, incorporated herein by reference, and may move the drill portion 1202 in yaw and pitch in the same manner.

The plurality of actuators, e.g., linear drive motor 1226, yaw motor 1223, and pitch motor 1227, are capable of moving the accessory 202 relative to the hand-held portion 1204 in at least three degrees of freedom including pitch, yaw, and depth. In one embodiment where the accessory 202 is a bur, the accessory drive motor 1216 acts as a fourth degree-of-freedom by selectively controlling the rotational speed of the accessory 202.

The drill portion 1202 supports the accessory 202 and one of the actuators and is movable by at least another of the actuators. Specifically, the drill portion 1202, and more specifically, the outer casing 1208, supports the linear drive motor 1226 and the accessory drive motor 1216. The linear drive motor 1226 translates the accessory 202 along the drill's depth axis Z. It should be appreciated that the drill portion 1202 is movable by the yaw motor 1223 and the pitch motor 1227. It should also be appreciated that the yaw motor 1223 and pitch motor 1227 move the accessory drive motor 1216 and the linear drive motor 1226 in pitch and yaw relative to the hand-held portion 1204. It should also be appreciated that the accessory drive motor 1216 can be controlled by the instrument driver 130 (FIG. 1A) or the motor controller 124 (FIG. 1B).

Figure 11B:
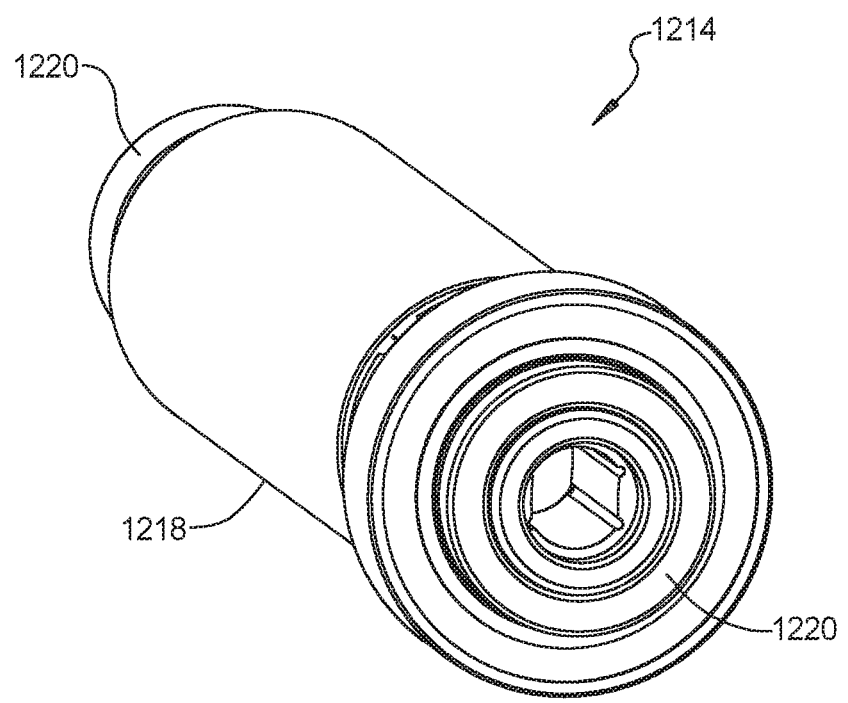
FIG. 11B is another perspective view of the bur drive rotor of FIG. 3.
Figure 15:
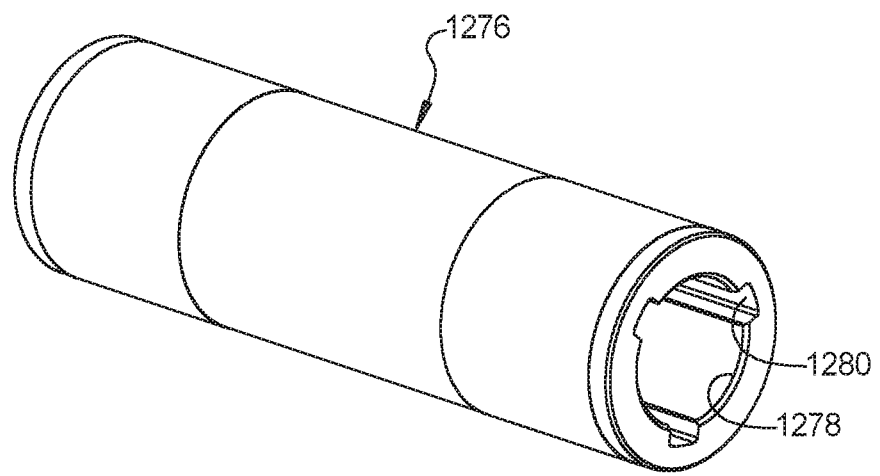
FIG. 15 is a perspective view of a bushing that cooperates with a nose tube of FIGS. 16A and 16B.
Figure 16A:
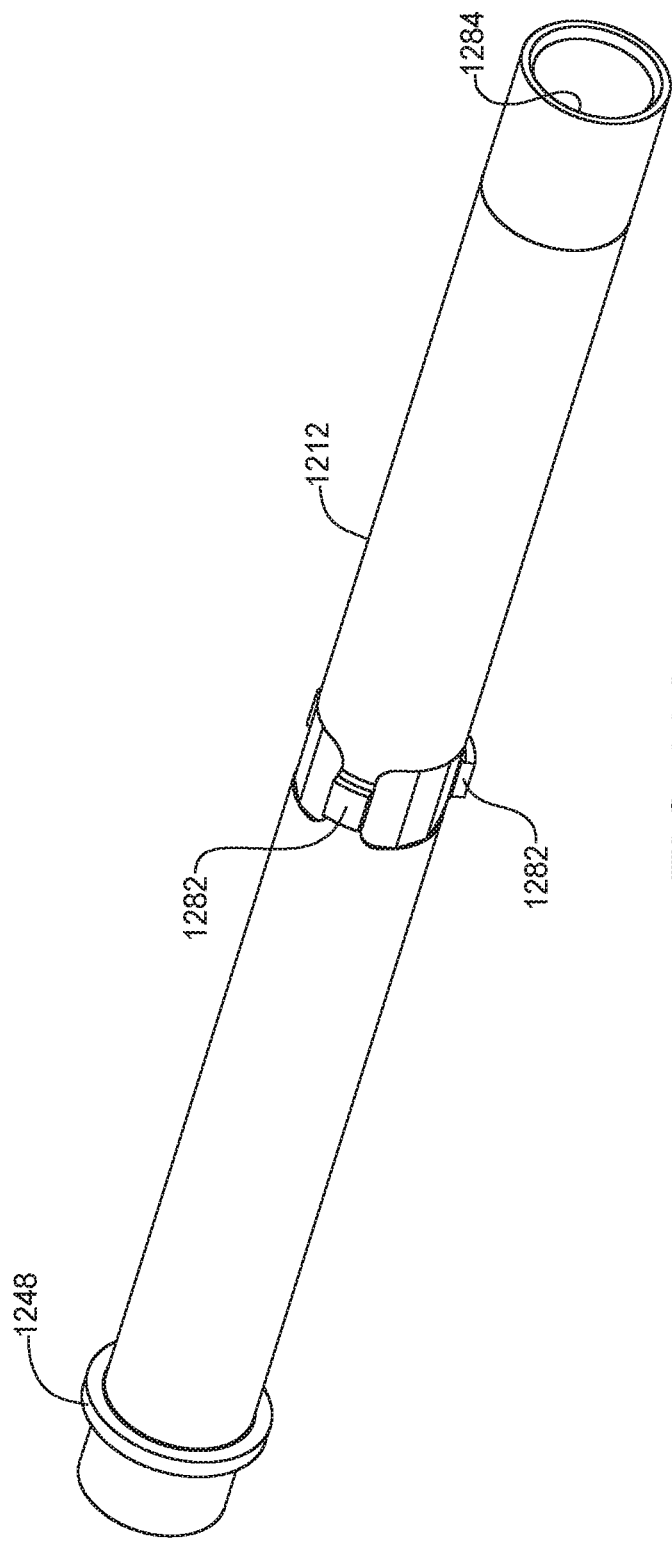
FIG. 16A is a perspective view of a nose tube of the drill portion of FIG. 2.
Figure 17:
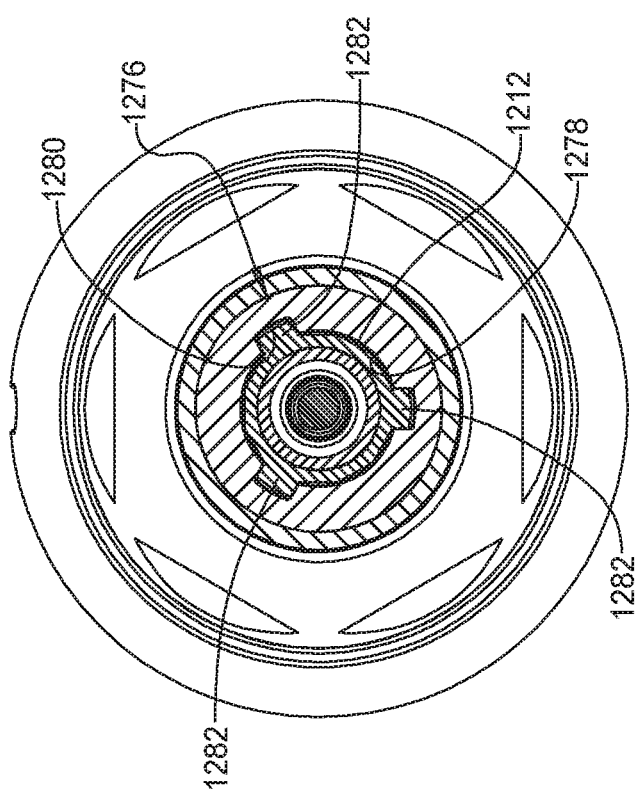
FIG. 17 is a sectional view taken along line 17-17 of FIG. 6.

In one embodiment, the accessory drive motor 1216 includes an electromagnetic coil 1217 and a rotor 1218 that is rotatably coupled to the outer casing 1208 to drive the accessory 202. The rotor 1218 can include at least one bearing 1220 at each end operatively engaging the outer casing 1208 via the electromagnetic coil 1217 to rotatably couple the rotor 1218 to the outer casing 1208 and allow rotation of the rotor 1218 relative to the outer casing 1208. It should be appreciated that the electromagnetic coil 1217 rotates the rotor 1218. It should be appreciated that the rotor 1218 drives an intermediate shaft 1224 via a double "D" connection as illustrated in FIG. 11B.

The drill portion 1202 may include any suitable means internal to the accessory drive motor 1216 and/or the linear drive motor 1226 to determine and control the position of the accessory 202. For example, one or more of the motors 1216, 1226 may be equipped with hall-effect sensors measuring signals based on the sensed magnet fields from the rotor and which vary as a function of the rotational position of the associated motor rotor. Additionally, or alternatively, rotary position encoders or absolute angular position encoders may be used.

Figure 5:
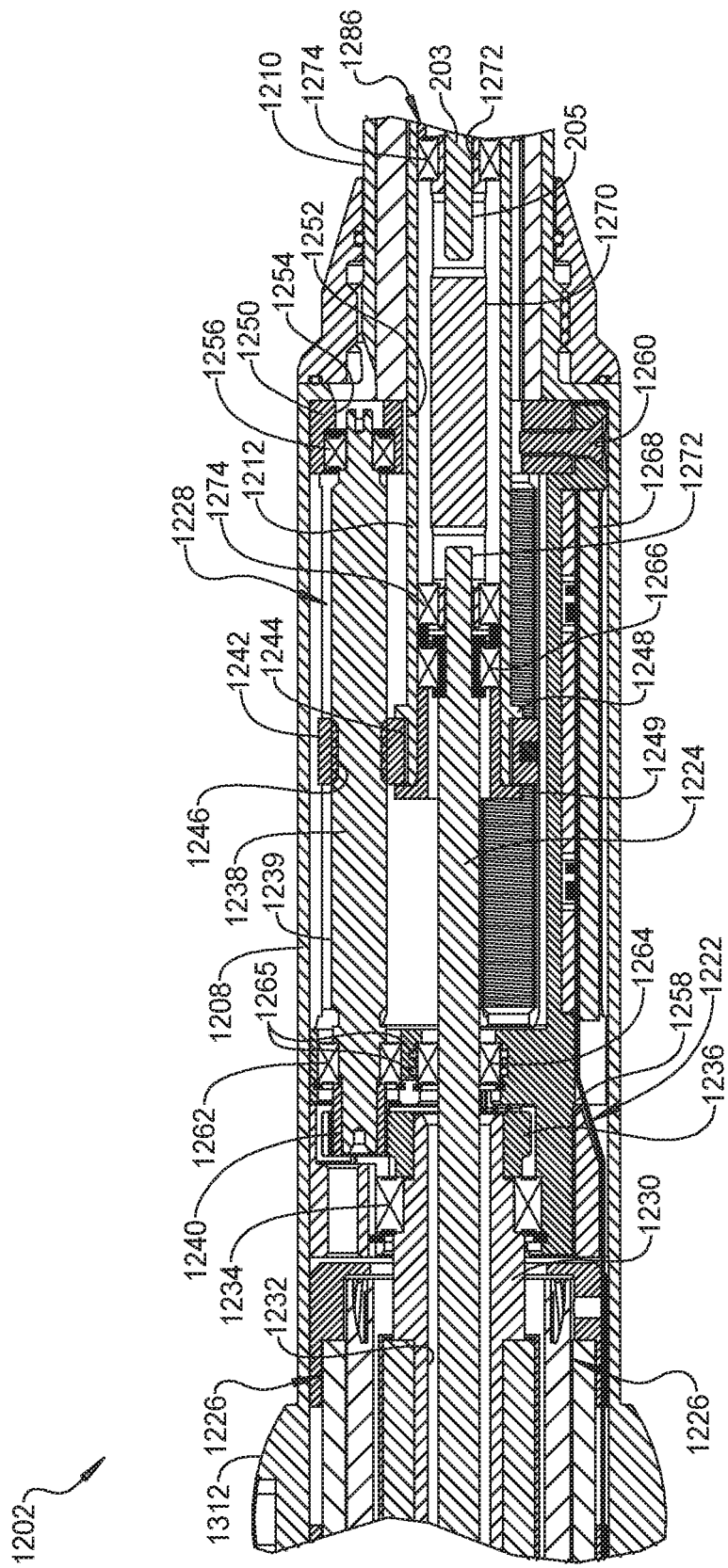
FIG. 5 is an enlarged cross-sectional view of yet another portion of the surgical instrument of FIG. 2.

Referring to FIGS. 2 and 5, the drill portion 1202 also includes a telescoping nose mechanism, generally indicated at 1222. The telescoping nose mechanism 1222 includes an intermediate shaft 1224 disposed in the outer casing 1208 and extending from the rotor 1218 for transmitting rotation from the accessory drive motor 1216 to the accessory 202 for driving the accessory 202. The telescoping nose mechanism 1222 also includes a linear drive motor, generally indicated at 1226, and a linear block (also referred to as an intermediate unit), generally indicated at 1228 cooperating with the linear drive motor 1226 to telescope or translate the nose tube 1212 along the linear or depth axis Z.

Referring to FIGS. 2, 4, 12, and 13, the linear drive motor 1226 includes an electromagnetic coil 1229 and a rotor 1230 having an aperture 1232 extending axially therethrough to allow the intermediate shaft 1224 to extend through the linear drive motor 1226 and be rotatably connected to the accessory drive motor 1216. The rotor 1230 can include at least one or more bearing 1234 engaging the outer casing 1208 via the electromagnetic coil 1229 at one end and the linear block 1228 at the other axial end. The linear drive motor 1226 also includes a drive gear 1236 at one end of the rotor 1230 to engage the linear block 1228. It should be appreciated that the electromagnetic coil 1229 rotates the rotor 1230. It should also be appreciated that the intermediate shaft 1224 has elongated flats 1225 at each axial end to form a double "D" connection.

Referring to FIGS. 2, 5, and 7-10, the linear block 1228 includes a plurality of leadscrews 1238 extending axially and spaced circumferentially. In the embodiment illustrated, there are three (3) leadscrews 1238. Each of the leadscrews 1238 has a plurality of threads 1239 therealong. Each of the leadscrews 1238 includes a driven pinion gear 1240 at one end thereof. The pinion gear 1240 includes a plurality of teeth to engage the teeth of the rotor's drive gear 1236.

The linear block 1228 also includes a carriage 1242 to move linearly or axially along the leadscrews 1238. The carriage 1242 extends from the nose tube 1212 and provides a mechanical interface between the leadscrews 1238 and the nose tube 1212. In one embodiment, the carriage 1242 is integrally formed as part of the nose tube 1212 such that they form part of a common component. In another embodiment, the carriage 1242 and the nose tube 1212 are separate components. The carriage 1242 includes threads 1247 to interface with the threads 1239 of the leadscrews 1238. The carriage 1242 may cooperate with the leadscrews 1238 according to various embodiments.

In one embodiment, the carriage 1242 includes a central aperture 1244 extending axially therethrough to receive the nose tube 1212. The carriage 1242 also includes a plurality of secondary apertures 1246 spaced radially from the central aperture 1244 and circumferentially and extending axially therethrough. The secondary apertures 1246 include the threads 1247 therein to engage the threads 1239 of the leadscrews 1238. The nose tube 1212 may have a flange 1248 extending radially to locate the carriage 1242 relative to the nose tube 1212 and a flanged bushing 1249 disposed in the nose tube 1212 and engaging the carriage 1242. It should be appreciated that all three pinion gears 1240 engaged with the drive gear 1236 results in coordinated motion of the three leadscrews 1238 as the linear drive rotor 1230 rotates.

The carriage 1242 may not have the central aperture 1244 depending on factors such as whether the carriage 1242 and nose tube 1212 are formed of the same component, and the like. Similarly, the secondary apertures 1246 may be replaced with alternative configurations, such as partially circular portions, rolling mechanisms (e.g., bearings), or the like, for interfacing with the threads 1239 of the leadscrews 1238.

The carriage 1242 is axially trapped or fixed at the proximal end of the nose tube 1212. The carriage 1242 and the nose tube 1212 may be configured to exhibit tight axial compliance such that the carriage 1242 does not wobble relative to the nose tube 1212 in the depth Z-axis direction. This axial compliance may be zero or so tight that there is effectively no tolerance that needs to be accounted for.

On the other hand, the nose tube 1212 and the carriage 1242 may be configured to enable relatively large radial compliance to adjust for tolerances. The radial compliance may be much greater than the tight axial compliance between the carriage 1242 and the nose tube 1212. Such radial compliance may be implemented in various manners. In one embodiment, an inner diameter of the central aperture 1244 of the carriage 1242 is deliberately larger than the outer diameter of the nose tube 1212 to provide a gap therebetween and allow the carriage 1242 to move radially with respect to the nose tube 1212. Additionally, or alternatively, the secondary apertures 1246, when present, may include an inner diameter being deliberately larger than the outer diameter of the leadscrews 1238. Furthermore, biasing members, such as springs, may be incorporated into the carriage 1241, and/or coupled between the carriage 1242 and the nose tube 1212. In other examples, the carriage 1242 and/or nose tube 1212 may be comprised of or have coupled thereto deformable materials for accommodating the radial movement.

The linear block 1228 also includes an end holder 1250 disposed about one end of the lead screws 1238. The end holder 1250 includes a central aperture 1252 extending axially therethrough to receive the nose tube 1212. The end holder 1250 also includes a plurality of secondary apertures 1254 spaced radially from the central aperture 1252 and circumferentially and extending axially therethrough. Each aperture 1254 includes a bearing 1256 to rotatably support one end of the leadscrews 1238. The end holder 1250 is disposed in the outer casing 1208 and is fixed relative thereto. The linear block 1228 also includes a housing 1258 disposed about the other end of the leadscrews 1238 and connected to the bearing 1234 disposed about the rotor 1230. The housing 1258 extends axially and is connected to the end holder 1250 by a plurality of fasteners 1260. The housing 1258 is disposed in the outer casing 1208 and is fixed relative thereto. It should be appreciated that the other end of the leadscrews 1238 are rotatably disposed in the housing 1250 by bearings 1262. It should also be appreciated that the intermediate shaft 1224 is rotatably supported in the housing 1258 by a bearing 1264. It should be appreciated that the intermediate shaft 1224 is supported in three locations and the middle bearing 1264 is supported by dual O-rings 1265. The distal end of the intermediate shaft 1224 is rotatably supported and axially fixed to the nose tube 1212 by a bearing 1266 (FIG. 5). This results in the intermediate shaft 1224 following the position of the nose tube 1212 as it telescopes in and out.

The linear block 1228 further includes a translation encoder 1268 disposed about the housing 1258 to sense the linear position of the carriage 1242. It should be appreciated that the translation encoder 1268 senses a position of the carriage 1242, which provides one method for the position of the nose tube 1212 and accessory 202 to be determined. This could be accomplished by placing a magnet on the carriage 1242 and one or more hall-effect sensors along the housing 1258. Other techniques for measuring or determining the position of the nose tube 1212 and accessory 202 may be utilized, such as electromagnetic sensors, or the like.

Referring to FIGS. 2, 5, 6, 14A, and 14B, the drive mechanism 1214 includes the interconnecting shaft 1270 disposed within the nose tube 1212 and interconnecting the distal end of the intermediate shaft 1224 and the proximal end 205 of the shaft 203 of the accessory 202. The interconnecting shaft 1270 has a double-D shape opening 1272 at each end as illustrated in FIG. 14A but can be any suitable shape without departing from the scope of the present invention. Each end of the interconnecting shaft 1270 is supported in the nose tube 1212 by a bearing 1274. It should be appreciated that the double-D shaped openings 1272 are connected to the keyed ends of the shafts 1224 and 203 such that rotation of the intermediate shaft 1224 is transmitted to the accessory shaft 203. It should also be appreciated that the interconnecting shaft 1270 transmits torque from the intermediate shaft 1224 to the accessory shaft 203 of the accessory 202.

Referring to FIGS. 2, 6, 15, and 17, the telescoping nose mechanism 1222 also includes a linear bushing 1276 disposed in the nose tube 1212. The bushing 1276 is generally cylindrical in shape with a generally circular cross-section. The bushing 1276 includes a central aperture 1278 extending axially therethrough to receive the nose tube 1212. The bushing 1276 also includes a plurality of internal channels or keyways 1280 extending radially from the central aperture and axially therealong for receiving the protrusions or external tabs 1282 of the nose tube 1212. Each internal keyway 1280 receives one of the external tabs 1282 of the nose tube 1212. The keyways 1280 extend parallel to the depth axis Z and are sized and shaped to restrain the external tabs 1282 to movement along the depth axis Z. The bushing 1276 may be formed from a different type of material than the casing 1208. The bushing 1276 may be formed of a material that provides a low-friction interface with the nose tube 1212 and may be formed of a non-magnetic material to allow for position sensing. It should be appreciated that the external tabs 1282 of the nose tube 1212 are keyed to the linear bushing 1276 to prevent rolling about its axis. It should also be appreciated that the bushing 1276 is fixed relative to the outer casing 1210.

Referring to FIGS. 2, 6, 16A, and 16B, the telescoping nose mechanism 1222 includes the nose tube 1212 extending axially and telescopes relative to the outer casing 1210. The nose tube 1212 is moved by the linear block 1228 along the depth axis Z relative to the outer casing 1210. It should be appreciated that, the external tabs 1282 slide in the keyways 1280, respectively, as the nose tube 1212 moves along the depth axis Z.

Referring to FIGS. 9, 10, 16A, and 16B, the telescoping nose mechanism 1222 includes an adapter or insert 1283 connected or inserted to the distal end 1284 of the nose tube 1212 by a suitable mechanism such as press-fitting. The insert 1283 has an external threaded portion 1285 at a distal end.

Figure 6:
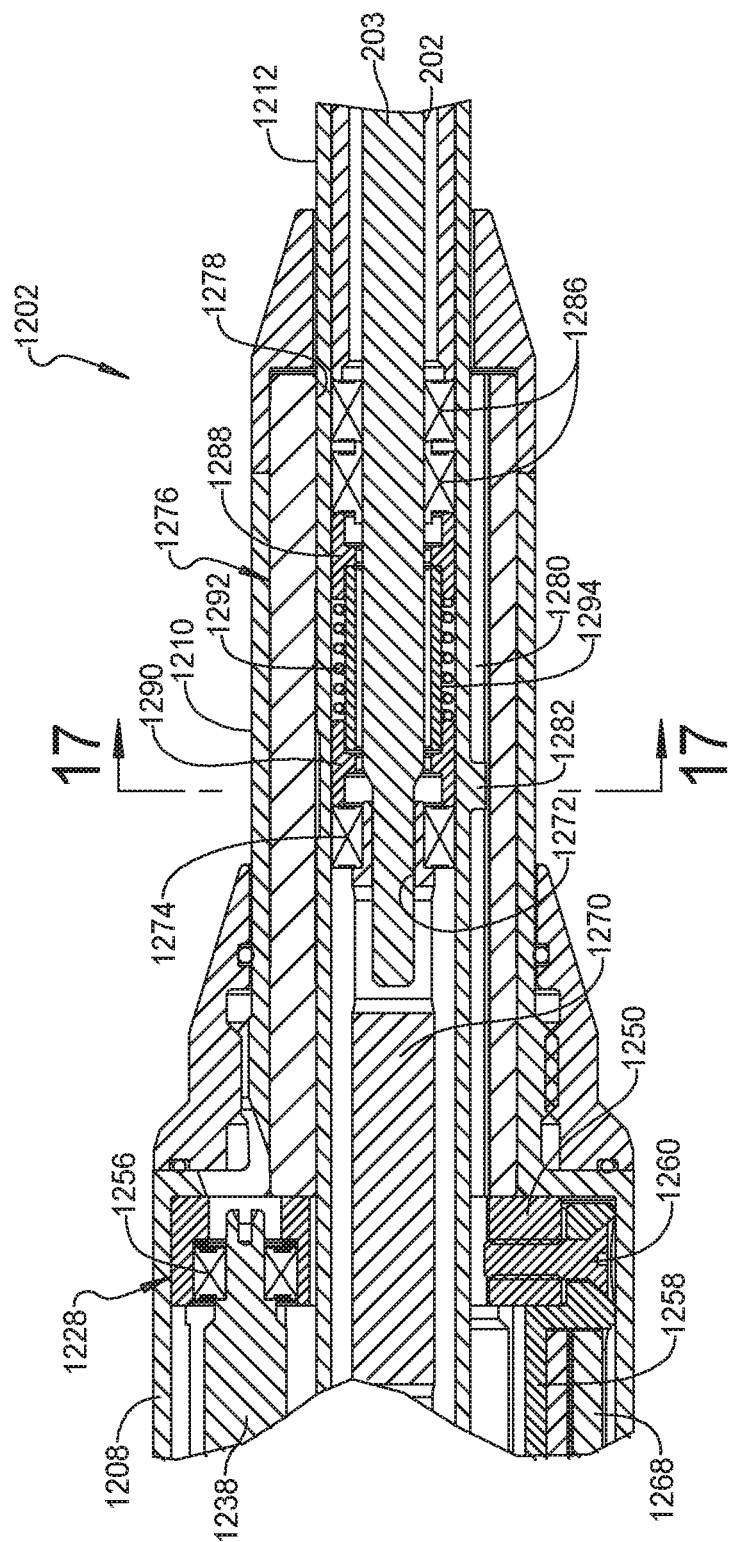
FIG. 6 is an enlarged cross-sectional view of a further portion of the surgical instrument of FIG. 2.
Figure 7:
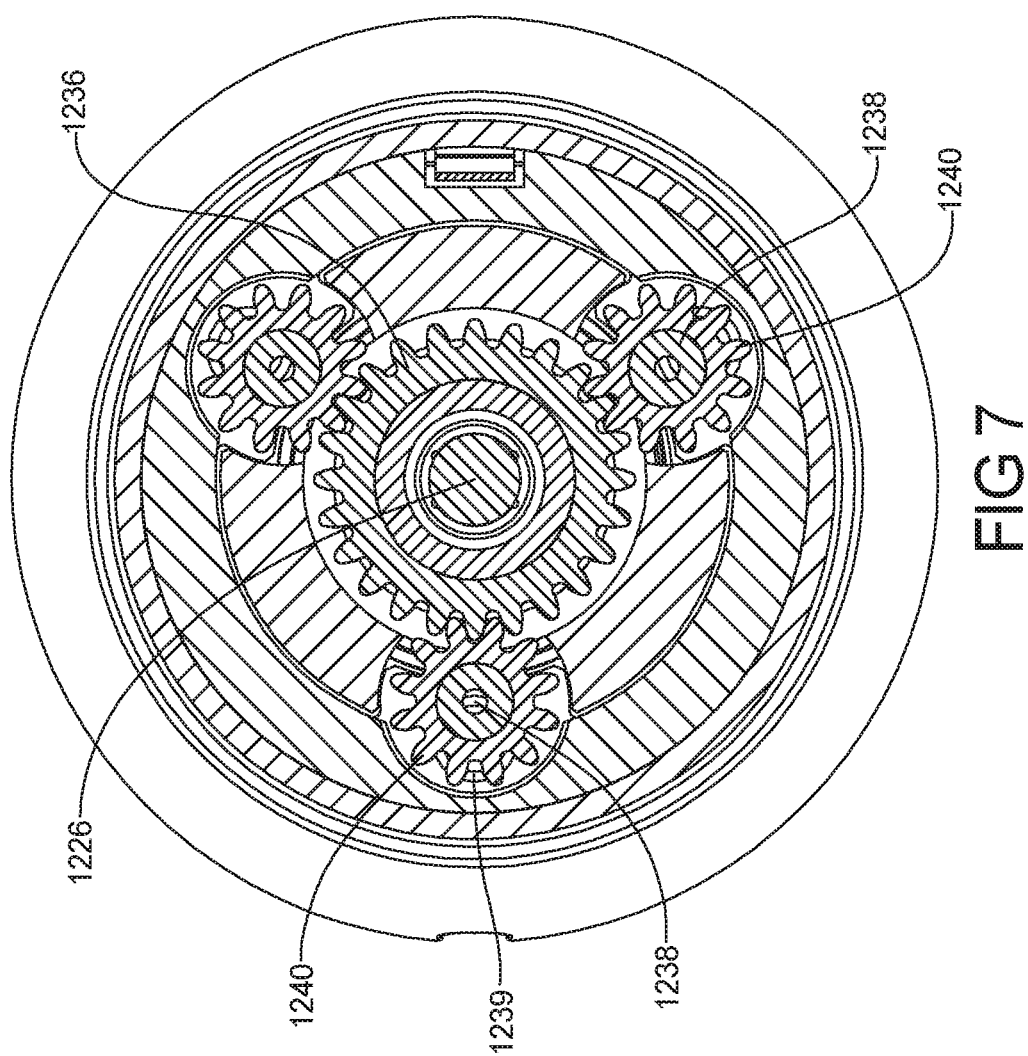
FIG. 7 is a sectional view taken along line 7-7 of FIG. 2.
Figure 8:
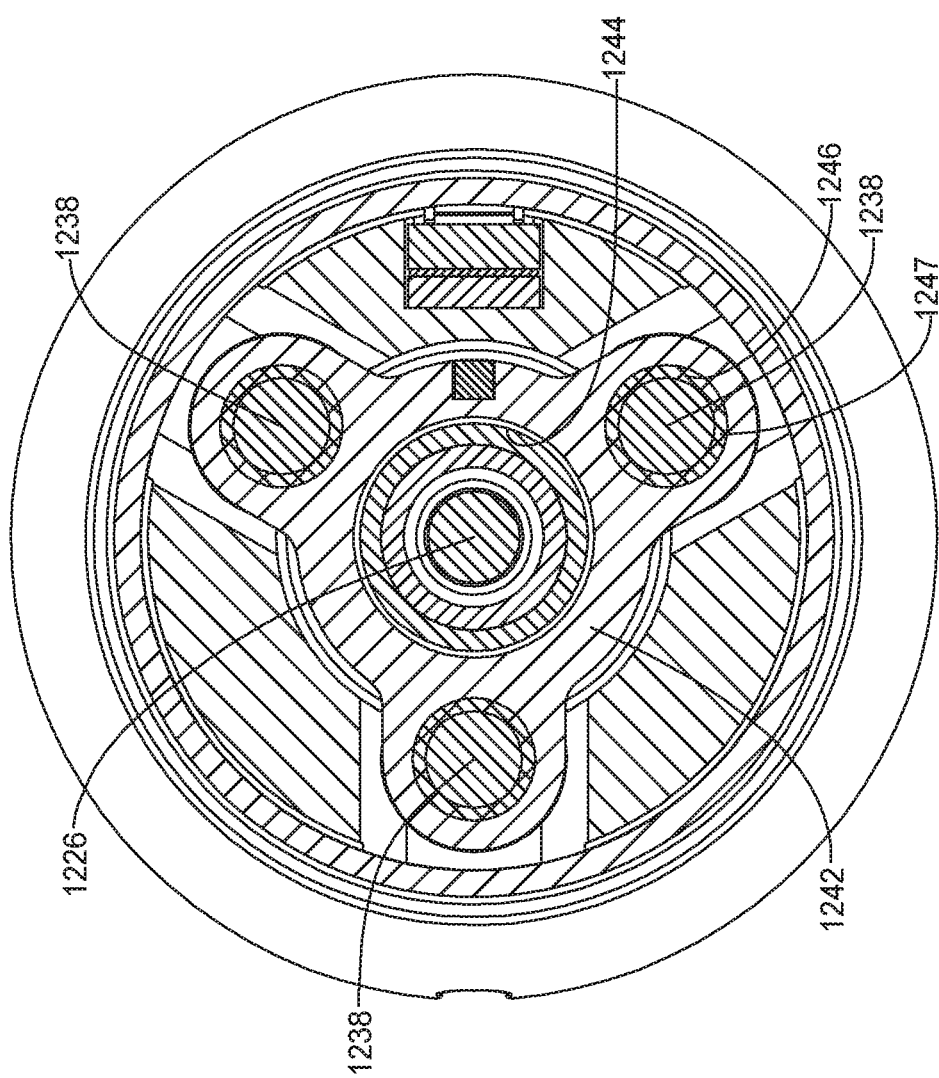
FIG. 8 is a sectional view taken along line 8-8 of FIG. 2.
Figure 9:
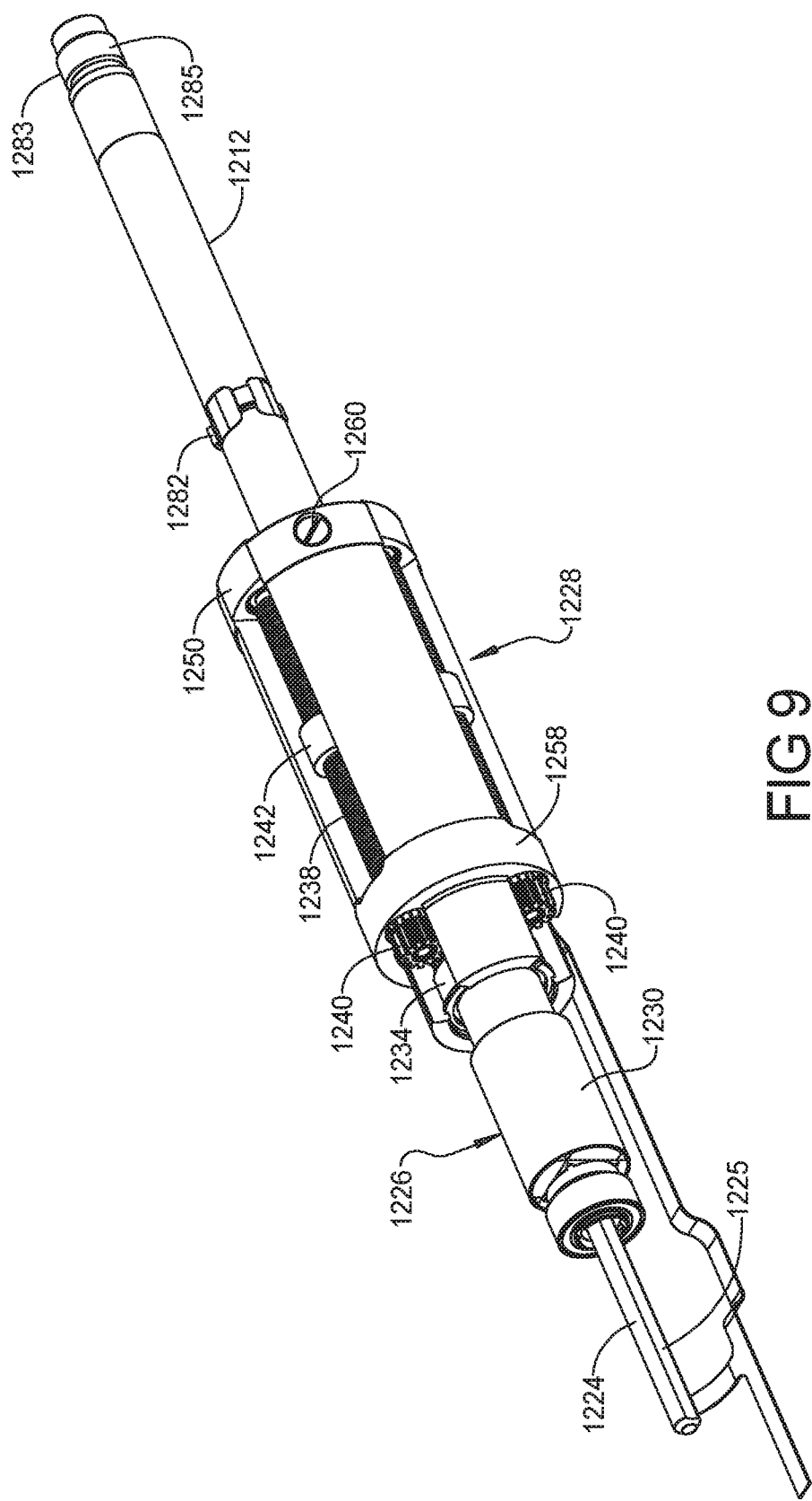
FIG. 9 is a perspective view of the linear drive section of the drill portion of the surgical instrument of FIG. 2 with outer housings and accessory removed.
Figure 10:
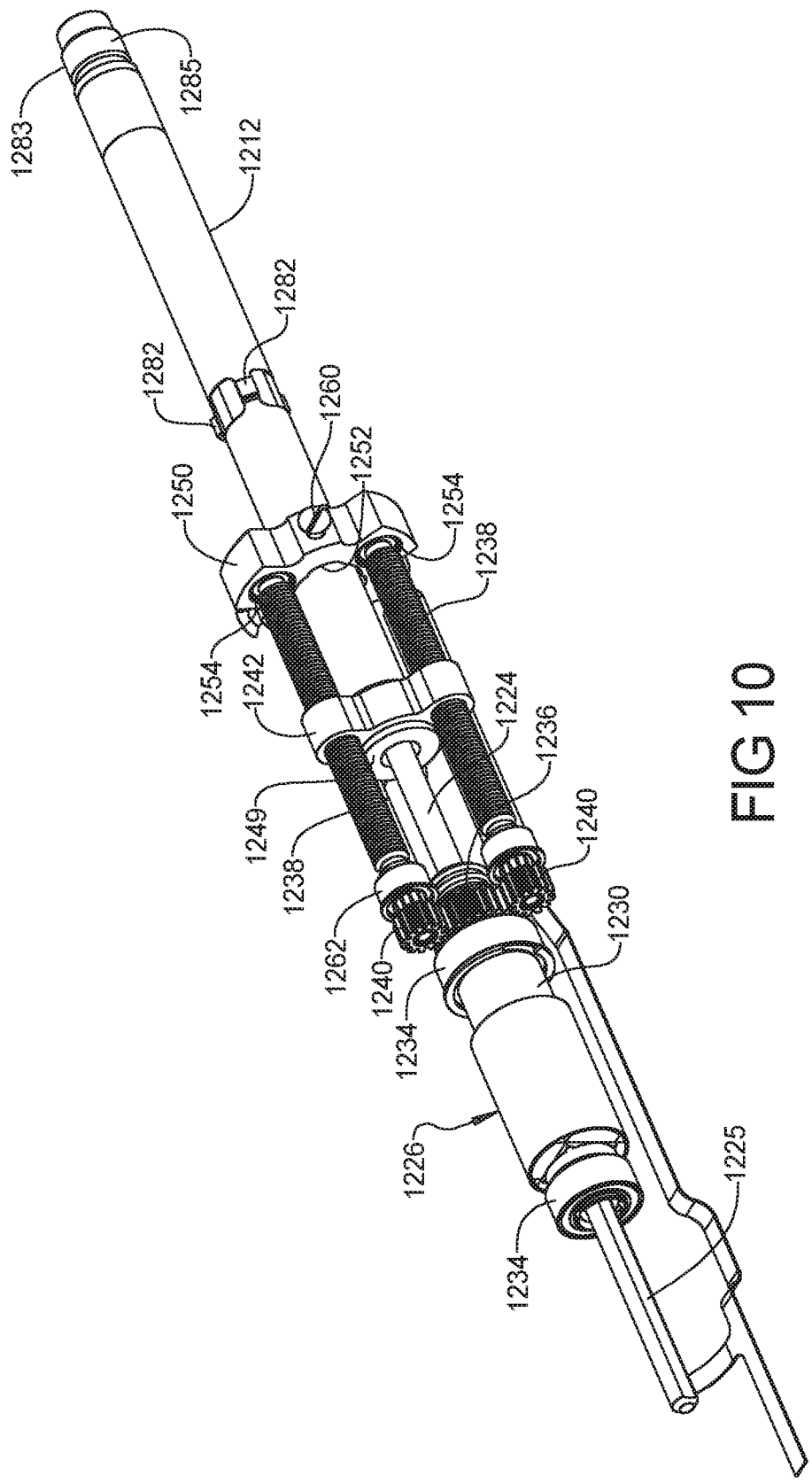
FIG. 10 is a view similar to FIG. 9 with a portion removed.

Referring to FIG. 6, the telescoping nose mechanism 1222 includes one or more bearings 1286 disposed inside the nose tube 1212 and configured to engage and rotatably support the accessory shaft 203 of the accessory 202. The telescoping nose mechanism 1222 also includes a plurality of spacers 1288 and 1294 disposed inside the nose tube 1212 and spaced axially by a spring 1292 therebetween to preload the numerous bearings within the nose tube 1212.

Figure 19:
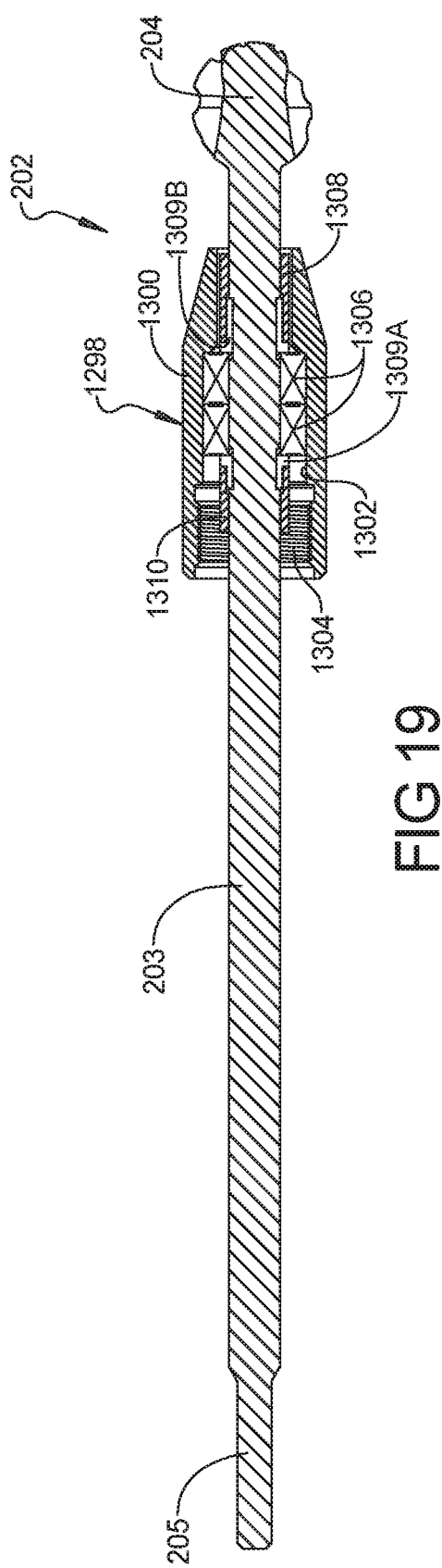
FIG. 19 is a cross-sectional view of the accessory of FIG. 18A.
Figure 20:
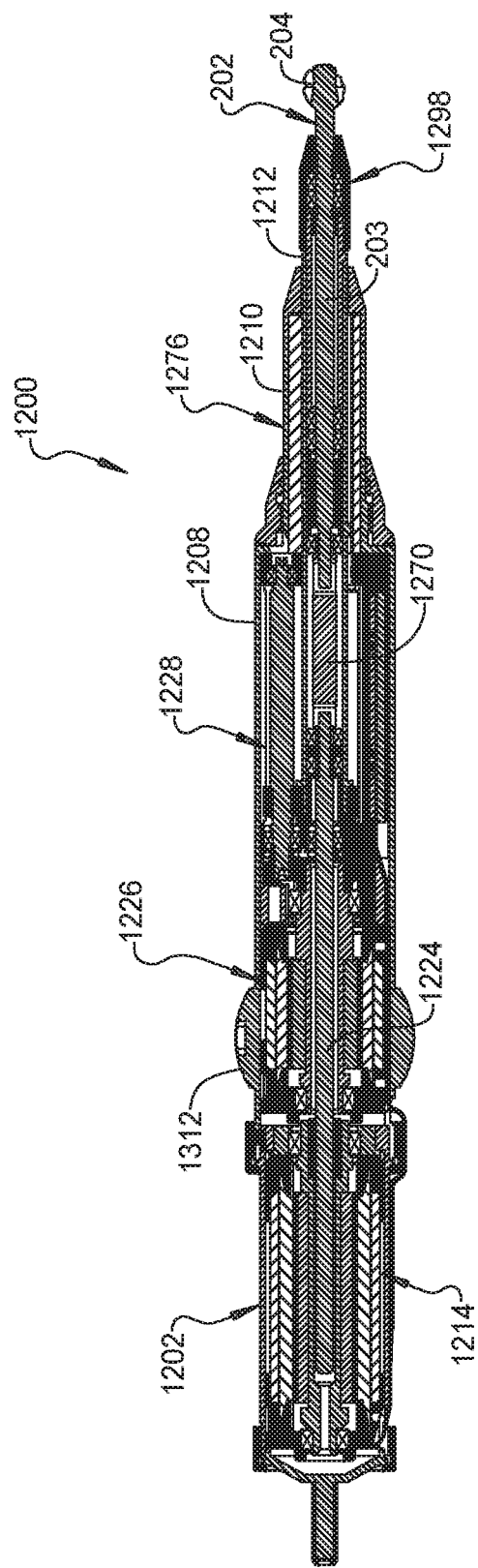
FIGS. 20-24 are individual cross-sectional views of the drill portion with the accessory of the surgical instrument in various positions along a depth axis.

Referring to FIGS. 18A, 18B, and 19, the accessory 202 may include a coupling ("bur") assembly 1298 to rotatably couple the accessory shaft 203 of the accessory 202 to the nose tube 1212 via the insert 1283 so that the accessory 202 rotates about the rotational axis R upon rotation relative to the nose tube 1212. The coupling assembly 1298 includes a connector 1300 having a bore 1302 extending axially therethrough with internal threads 1304 at one end to retain the coupling assembly 1298 to the threaded end 1285 of the insert 1283. The coupling assembly 1298 also includes one or more bearings 1306 disposed in the bore 1302 between the connector 1300 and the accessory shaft 203 of the accessory 202 to allow rotation therebetween. The coupling assembly 1298 also includes flanged clam shells 1309A and 1309B to trap or capture inner races of the bearings 1306 in place relative to the accessory shaft 203. The coupling assembly 1298 also includes sleeves 1308 and 1310 disposed on the accessory shaft 203 about the flanged clam shells 1309A and 1309B. It should be appreciated that the above embodiment of the coupling assembly 1298 should not be considered limiting. It should also be appreciated that alternative methods for securing the coupling assembly 1298 to the nose tube 1212 are permissible as well as alternative manufacturing methods for securing the inner races of the bearing 1306 in place relative to the accessory shaft 203. It should further be appreciated nose tube 1212 supports the accessory 202 and is movable relative to the casings 1208 and 1210 in translation along the depth axis Z, i.e., the nose tube 1212, which is typically cylindrical, adjusts the position of the accessory 202 along the depth axis Z.

Figure 21:
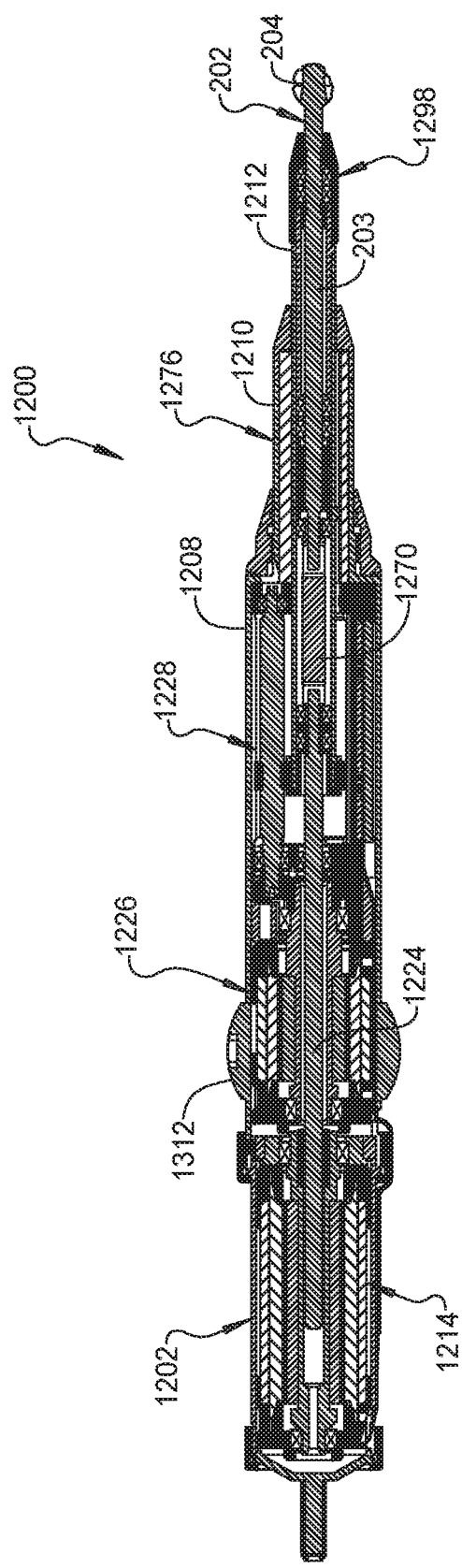
Figure 22:
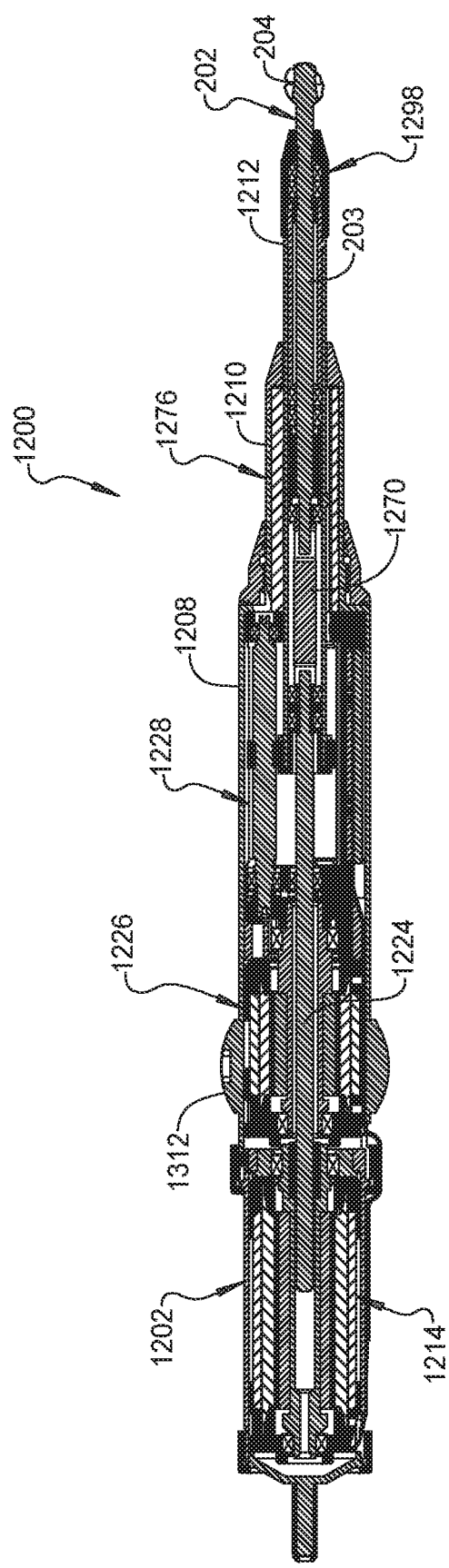
Figure 23:
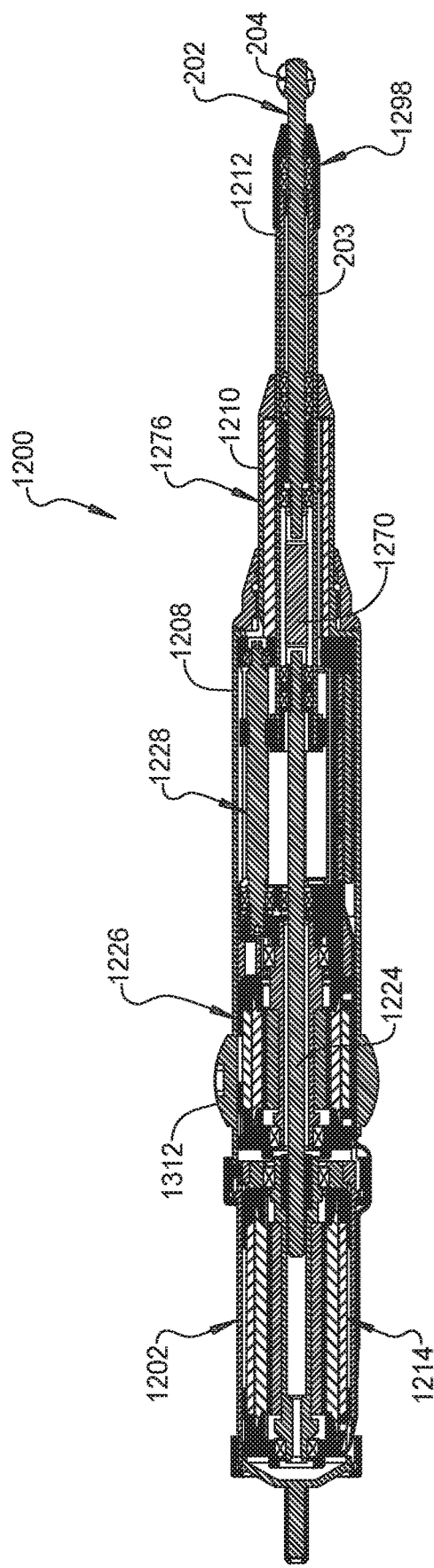
Figure 24:
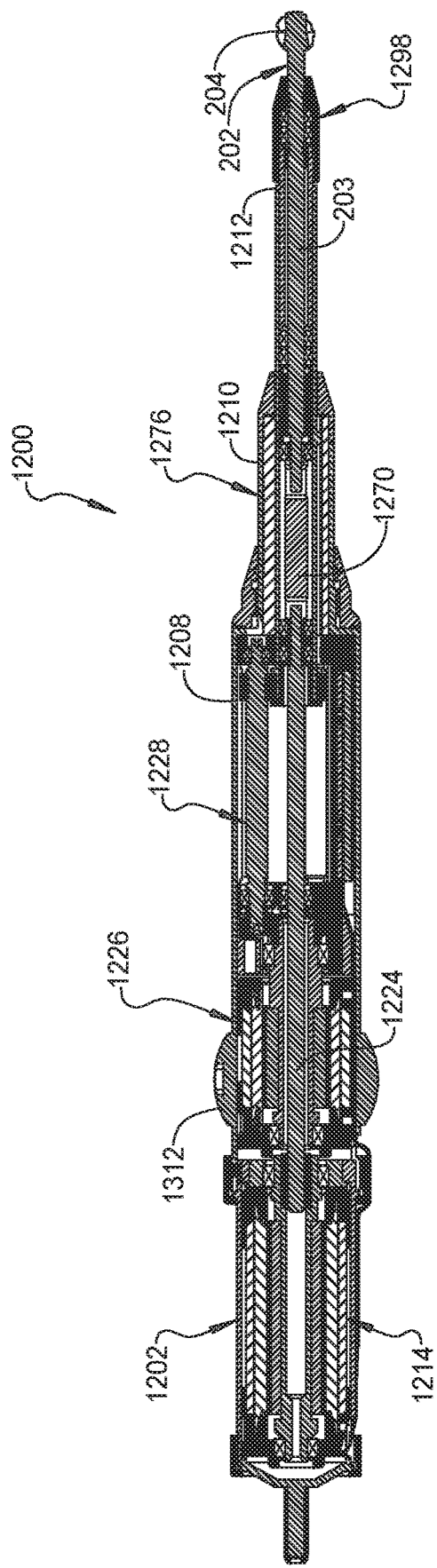
Figure 25:
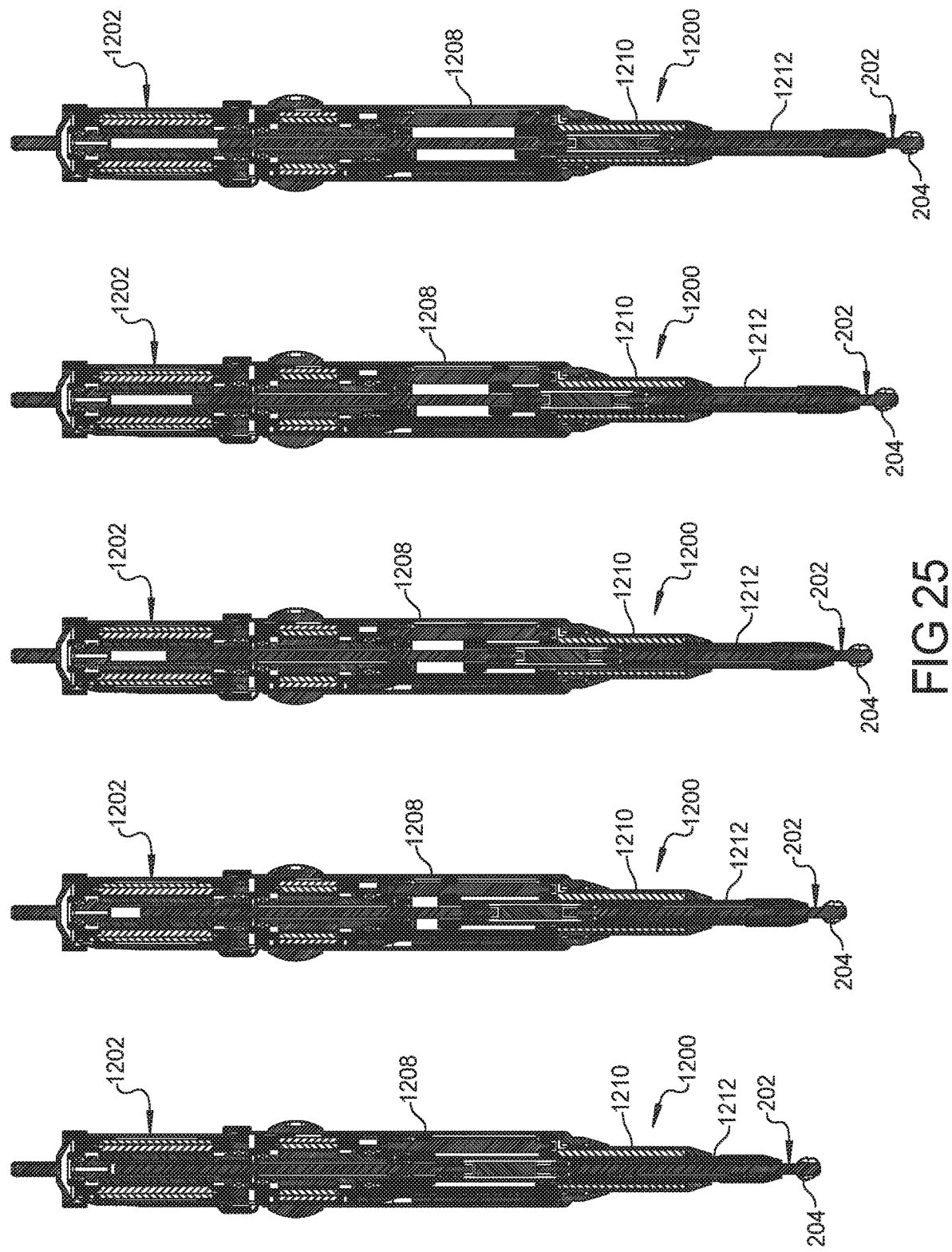
FIG. 25 is a compilation of cross-sectional views of the drill portion of FIGS. 20-24 with the accessory of the surgical instrument in various positions along the depth axis.

FIGS. 20-25, for example, show the nose tube 1212 moved to different locations relative to the outer casings 1208 and 1210 along the depth axis Z. Specifically, in FIG. 20 the nose tube 1212 is nearly fully retracted, and in FIG. 24, the nose tube 1218 is nearly fully extended. FIGS. 21-23 show a position between those shown in FIGS. 20 and 24. Specifically, FIG. 22 shows the nose tube 1212 in a "home" position. FIG. 21 shows the nose tube 1212 in an intermediate position between the fully retracted position and the home position. FIG. 23 shows the nose tube 1212 in an intermediate position between the home position and the fully extended position. FIG. 25 shows all of the positions illustrated in FIGS. 20-25. It should be appreciated that, when the nose tube 1212 moves relative to the casings 1208 and 1210, the coupling assembly 1298, the accessory 202, and all other components housed in the nose tube 1212 move with the nose tube 1212 as well as the intermediate shaft 1224.

As illustrated in FIG. 2, the drill portion 1202 includes a gimbal 1312 to support movement of the accessory 202 in at least two pivoting degrees of freedom relative to the hand-held portion 1204. Specifically, the accessory 202 is adjustable in pitch and yaw about the gimbal 1312. The gimbal 1312 is fixed along the depth axis Z relative to the hand-held portion 1204. It should be appreciated that the nose tube 1212 translates linearly relative to the gimbal 1312 along the drill's depth axis Z.

The gimbal 1312 is integrated into the outer casing 1208 of the drill portion 1202 so the drill portion 1202 and the accessory 202 are able to pivot relative to the hand-held portion 1204. The gimbal 1312 may be located around the approximate center of gravity G of drill portion 1202 to minimize the mass moment of inertia of the drill portion 1202 as the drill portion 1202 is pivoted to maximize the angular acceleration for a given supplied torque.

In one embodiment, a trigger or foot pedal, or alternatively a button, (not shown) can be supported by the outer casing 1206 of the hand-held portion 1204 to power the accessory drive motor 1214, i.e., to selectively supply power to or not supply power to the accessory 202. As set forth above with respect to surgical instrument 1200, the surgical instrument 1200 may include a sensor (not shown) disposed inside the surgical instrument 1200. The sensor generates a signal if the trigger is actuated and/or not actuated. The output signals from the sensor are forwarded by a data connection 123 (FIG. 1A) to instrument driver console 130. Based on the state of this sensor signal, the instrument driver 130 applies energization signals to the accessory drive motor 1214 when the distal end tip 204 of the accessory 202 is in the boundary 106 of target volume 104. In the alternative to, or in addition to the trigger or button, a foot pedal (not shown) can be in communication with the instrument controller 120 to control the accessory drive motor 1214 by providing on/off instructions to the accessory drive motor 1214.

As set forth above, in some embodiments, when the distal end tip 204 of the accessory 202 is outside of the boundary 106 of the target volume 104, the instrument driver 120 does not apply an energization signal to the accessory drive motor 1214 even if the trigger is actuated. The tracking and control system 100 can be configured such that the instrument driver console 130 applies an energization signal to reduce the speed of the accessory 202 when the distal end tip 204 of the accessory 202 enters the buffer 105 of the target volume 104 or as the range of motion of the tool is consumed.

Other control systems/methods for controlling movement/operation of the accessory 202 can be like those described in U.S. Patent Application Publication No. 2013/0060278, filed Aug. 31, 2012, entitled "SURGICAL INSTRUMENT INCLUDING HOUSING, A CUTTING ACCESSORY THAT EXTENDS FROM THE HOUSING AND ACTUATORS THAT ESTABLISH THE POSITION OF THE CUTTING ACCESSORY RELATIVE TO THE HOUSING," hereby incorporated by reference.

Embodiments of the present invention have been described in an illustrative manner. It is to be understood that the terminology, which has been used, is intended to be in the nature of words of description rather than of limitation.

Many modifications and variations of the present invention are possible in light of the above teachings. Therefore, within the scope of the appended claims, the present invention may be practiced other than as specifically described.

The invention claimed is:

1. A surgical instrument comprising:
a hand-held portion configured to be manipulated by a user;
a pivoting portion operatively coupled to said hand-held portion and being configured to pivot with respect to said hand-held portion according to first and second degrees of freedom; and
wherein said pivoting portion includes an accessory drive motor coupled with and being configured to rotate an intermediate shaft, and said pivoting portion includes a telescoping nose mechanism including:
a nose tube;
an intermediate unit including:
a plurality of leadscrews each comprising a first end and a driven gear fixed at said first end; and
a carriage extending from said nose tube and including a central aperture axially extending through said carriage, and said carriage being configured to interface with and linearly translate along each of said leadscrews;
a linear drive motor configured to rotate a drive gear, said drive gear configured to cooperate with each of said driven gears to enable rotation of each of said leadscrews to linearly translate said carriage and said nose tube relative to said hand-held portion with respect to a third degree of freedom; and
wherein said intermediate shaft extends through and is configured to rotate within said central aperture of said carriage.

2. The surgical instrument of claim 1, wherein said carriage is threaded to interface with threads on said leadscrews.

3. The surgical instrument of claim 1, wherein said carriage receives said nose tube and includes a plurality of second apertures spaced radially from said central aperture for receiving and cooperating with said leadscrews.

4. The surgical instrument of claim 3, wherein said second apertures are threaded to cooperate with threads on said leadscrews.

5. The surgical instrument of claim 1, wherein said carriage and said nose tube are separate components.

6. The surgical instrument of claim 1, wherein said carriage is coupled to one end of said nose tube.

7. The surgical instrument of claim 1, wherein said nose tube and said carriage are axially fixed relative to each other.

8. The surgical instrument of claim 1, wherein an inner diameter of the central aperture is larger than an outer diameter of the nose tube to provide a gap therebetween, enabling the carriage to move radially with respect to the nose tube.

9. The surgical instrument of claim 1, wherein said nose tube includes a plurality of external tabs extending radially therefrom.

10. The surgical instrument of claim 9, wherein said telescoping nose mechanism includes a linear bushing cooperating with said nose tube and including a central aperture extending axially therethrough and a plurality of internal keyways extending radially from said central aperture and extending axially therealong to receive said external tabs of said nose tube.

11. The surgical instrument of claim 1, wherein said nose tube is configured to operatively support an accessory.

12. The surgical instrument of claim 11, wherein said linear drive motor is configured to linearly translate the accessory relative to said hand-held portion with respect to said third degree of freedom and wherein said linear drive motor is axially fixed relative to said pivoting portion.

13. The surgical instrument of claim 11, including a coupling assembly coupled to said nose tube and being configured to support the accessory wherein said coupling assembly includes a connector having a bore to enable a shaft of the accessory to extend therethrough.

14. The surgical instrument of claim 11, wherein said accessory drive motor includes an electromagnetic coil and a rotor rotatable by said electromagnetic coil and having an aperture extending through said rotor to enable said intermediate shaft to extend through said rotor.

15. The surgical instrument of claim 11, wherein said nose tube includes an interconnecting shaft having a first end coupled to said intermediate shaft and a second end being configured to couple to a shaft of the accessory to enable driving of the accessory.

16. The surgical instrument of claim 15, wherein each of said first and second ends of said interconnecting shaft has a double-D shaped opening such that said first end is configured to receive a mating end of said intermediate shaft and such that said second end is configured to receive a mating end of the shaft of the accessory.

17. The surgical instrument of claim 11, wherein said telescoping nose mechanism includes an internal bearing disposed within said nose tube and being configured to support movement of a shaft of the accessory.

18. The surgical instrument of claim 1, further comprising a casing supporting said telescoping nose mechanism and with said nose tube being configured to linearly translate relative to said casing with respect to said third degree of freedom.

19. The surgical instrument of claim 1, wherein each of said plurality of leadscrews further comprises a second end opposite said first end, and wherein said intermediate unit further comprises an end holder comprising a central aperture extending therethrough to receive said nose tube and a plurality of second apertures spaced radially from said central aperture and each of said second apertures of said end holder comprises a bearing for rotatably supporting said second end of one of said leadscrews.

20. The surgical instrument of claim 19, wherein each of said leadscrews is linearly fixed between said drive gear and said end holder such that each of said leadscrews are linearly fixed relative to said pivoting portion.

21. The surgical instrument of claim 1, wherein the drive gear has an aperture extending axially through said drive gear and wherein said intermediate shaft extends through and is configured to rotate within said aperture of said drive gear.

* * * * *